US012590946B2

(12) United States Patent
Furusato et al.

(10) Patent No.: US 12,590,946 B2
(45) Date of Patent: * Mar. 31, 2026

(54) TEST STRIP CONTAINER AND TEST STRIP DISCHARGING MECHANISM

(71) Applicant: ARKRAY, Inc., Kyoto (JP)

(72) Inventors: Noriaki Furusato, Kyoto (JP); Yusuke Wada, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 718 days.

This patent is subject to a terminal disclaimer.

(21) Appl. No.: 18/053,713

(22) Filed: Nov. 8, 2022

(65) Prior Publication Data

US 2023/0152299 A1 May 18, 2023

(30) Foreign Application Priority Data

Nov. 12, 2021 (JP) ................................. 2021-185193

(51) Int. Cl.
*G01N 35/04* (2006.01)
*G01N 33/487* (2006.01)
(52) U.S. Cl.
CPC . *G01N 33/48778* (2013.01); *G01N 33/48757* (2013.01)
(58) Field of Classification Search
CPC ....... G01N 33/48778; G01N 33/48757; G01N 2035/00039; G01N 2035/00089;
(Continued)

(56) References Cited

U.S. PATENT DOCUMENTS

| | | | |
|---|---|---|---|
| 8,535,618 B1 | 9/2013 | Werner | |
| 2002/0057993 A1* | 5/2002 | Maisey | ............ G01N 33/48757 |
| | | | 422/430 |
| 2005/0281706 A1 | 12/2005 | Funke et al. | |

FOREIGN PATENT DOCUMENTS

| | | |
|---|---|---|
| JP | H05-5736 A | 1/1993 |
| JP | H05-264540 A | 10/1993 |

(Continued)

OTHER PUBLICATIONS

The extended European search report issued by the European Patent Office on Mar. 21, 2023, which corresponds to European Patent Application No. 22206388.5-1001 and is related to U.S. Appl. No. 18/053,713.

(Continued)

*Primary Examiner* — Charles Capozzi
*Assistant Examiner* — Michael Stanley Gzybowski
(74) *Attorney, Agent, or Firm* — Studebaker Brackett PLLC

(57) ABSTRACT

A test strip container includes: an accommodating member in which a test strip is accommodated; a moving member moving the test strip therein; a door member opening and closing at a side surface of the accommodating member to discharge the test strip out of the accommodating member, and cutting the interior and the exterior of the accommodating member off from each other when closed; a door accommodating portion covering the door member, in which the door member can open and close; and a discharge opening cutting the interior and an exterior of the door accommodating portion off from each other when closed, and is provided at the door accommodating portion so as to open and close to discharge the test strip to the exterior of the door accommodating portion, the discharge opening
(Continued)

being able to open when the accommodating member is closed by the door member.

8 Claims, 26 Drawing Sheets

(58) Field of Classification Search
CPC ........... G01N 35/00029; G01N 33/493; G01N 2035/00118; G01N 33/4875; G01N 35/04; B01L 2300/042; B01L 2300/0825; B01L 2300/0832; B01L 2300/10; B01L 9/52
See application file for complete search history.

(56) References Cited

FOREIGN PATENT DOCUMENTS

| | | | |
|---|---|---|---|
| JP | 2004-507763 | A | 3/2004 |
| WO | 02/18940 | A2 | 3/2002 |
| WO | 2006/000792 | A1 | 1/2006 |

OTHER PUBLICATIONS

"Notice of Reasons for Refusal" Office Action issued in JP 2021-185193; mailed by the Japanese Patent Office on Jan. 21, 2025.

* cited by examiner

TEST STRIP CONTAINER AND TEST STRIP DISCHARGING MECHANISM

CROSS-REFERENCE TO RELATED APPLICATION

This application claims priority under 35 USC 119 from Japanese Patent Application No. 2021-185193, filed on Nov. 12, 2021, the disclosure of which is incorporated by reference herein.

BACKGROUND

Technical Field

The present invention relates to a test strip container and a test strip discharging mechanism.

Related Art

In order to carry out measurement continuously by using test strips that are used to measure a predetermined item included in a sample of urine or the like, a mechanism is used that inserts plural test strips into a device, and takes the inserted test strips out one-by-one. A specimen is applied to the test strip that is taken out by the mechanism, and the predetermined item is measured.

For example, in the technique disclosed in Japanese Patent Application Laid-Open (JP-A) No. H05-264540, an "in-drum claw portion" is provided at a drum container. While the drum container is rotatingly driven, testing papers that are stored therein catch on this "in-drum claw portion" one-by-one, and are dropped onto a sorter rack. Further, for example, in the automatic urine testing device disclosed in JP-A No. H05-5736, even if a reagent portion 20a on a urine testing paper deteriorates by absorbing humidity of an allowable amount or more, in order to solve the problem that the automatic urine testing device cannot sense the deterioration of the reagent portion 20a, a reagent portion for sensing intermediate deterioration of the urine testing paper is provided, and detecting means for optically detecting the deterioration of the reagent portion for urine testing is provided.

In order to discharge test strips out to the exterior of a container as in the technique of JP-A No. H05-264540, an opening portion must be provided at the container. However, while the opening portion is open, outside air that includes water vapor flows into the container interior from the container exterior, and therefore, there is the concern that the test strips will deteriorate. Further, in a case of providing a reagent portion for sensing intermediate deterioration of a urine testing paper as in the technique of JP-A No. H05-5736, the cost of the urine test strip increases. Moreover, even if a reagent portion for sensing intermediate deterioration of the urine testing paper is provided, it cannot at all resist deterioration of the urine test strip due to humidity. Note that, in both of the techniques of JP-A No. H05-264540 and JP-A No. H05-5736, measures are taken at the test strip containers such that as little as possible outside air enters into the interior of the accommodating member. However, in these techniques, outside air cannot be prevented from entering into the accommodating member from the opening portion at the time of discharging a test strip from the accommodating member.

SUMMARY

The present disclosure provides a mechanism that can discharge a test strip while preventing entry of outside air into a container that accommodates test strips.

A test strip container of an aspect of the present disclosure has an accommodating member, a moving member, a door member, a door accommodating portion, and a discharge opening. A test strip is accommodated at the interior of the accommodating member. The moving member moves the test strip at the interior of the accommodating member. The door member is provided so as to be able to open and close at the side surface of the accommodating member, in order to discharge the test strip, which has been moved by the moving member, to the exterior of the accommodating member. Moreover, at a time of being closed, the door member cuts the interior and the exterior of the accommodating member off from each other. The door accommodating portion covers the door member from the outer side of the accommodating member. The door member can open and close at the interior of the door accommodating portion. The discharge opening, at a time of being closed, cuts the interior and the exterior of the door accommodating portion off from each other. The discharge opening is provided at the door accommodating portion so as to be able to open and close, in order to discharge the test strip, which has been discharged to the exterior of the accommodating member, to the exterior of the door accommodating portion. Further, the discharge opening is configured so as to be able to open in the state in which the accommodating member is closed by the door member.

Because the aspect of the present disclosure is structured as described above, there is provided a mechanism that can discharge a test strip while preventing entry of outside air into a container that accommodates test strips.

BRIEF DESCRIPTION OF THE DRAWINGS

Exemplary embodiments will be described in detail based on the following figures, wherein.

DETAILED DESCRIPTION

Figure 1:
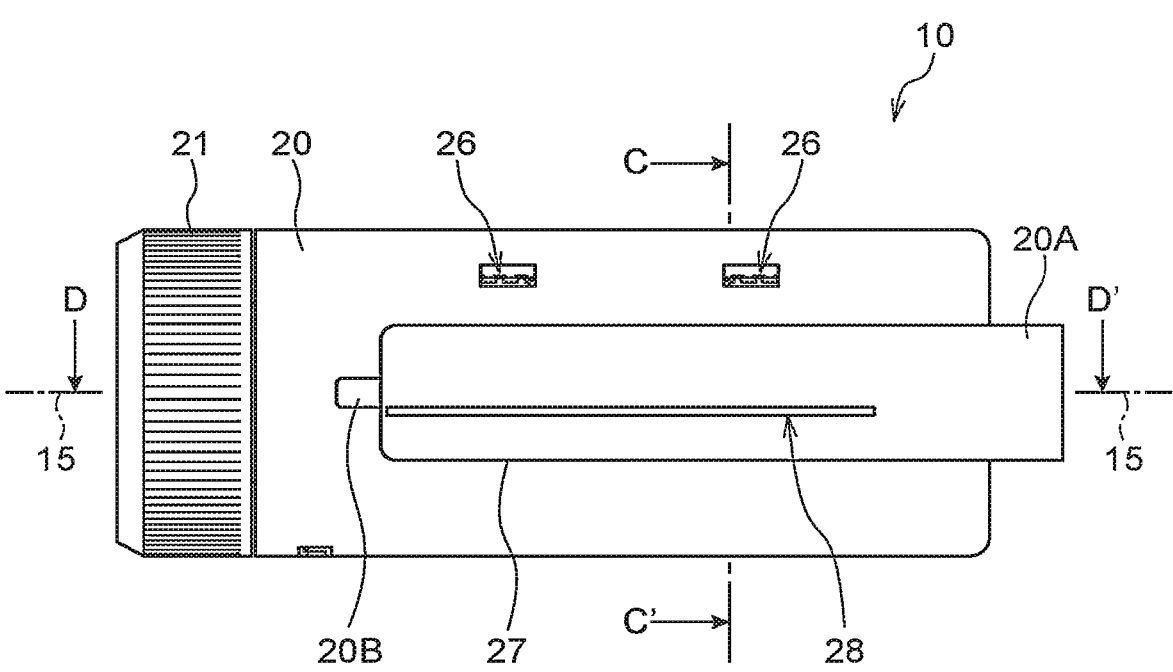
FIG. 1 illustrates a test strip container of an exemplary embodiment in a front view.

Exemplary embodiments of the present disclosure are described hereinafter with reference to the drawings. Note that reference numerals that are used in common in the respective drawings indicate the same objects even if not stated in the following descriptions of the respective drawings.

(1) Exemplary Embodiment

Figure 2:
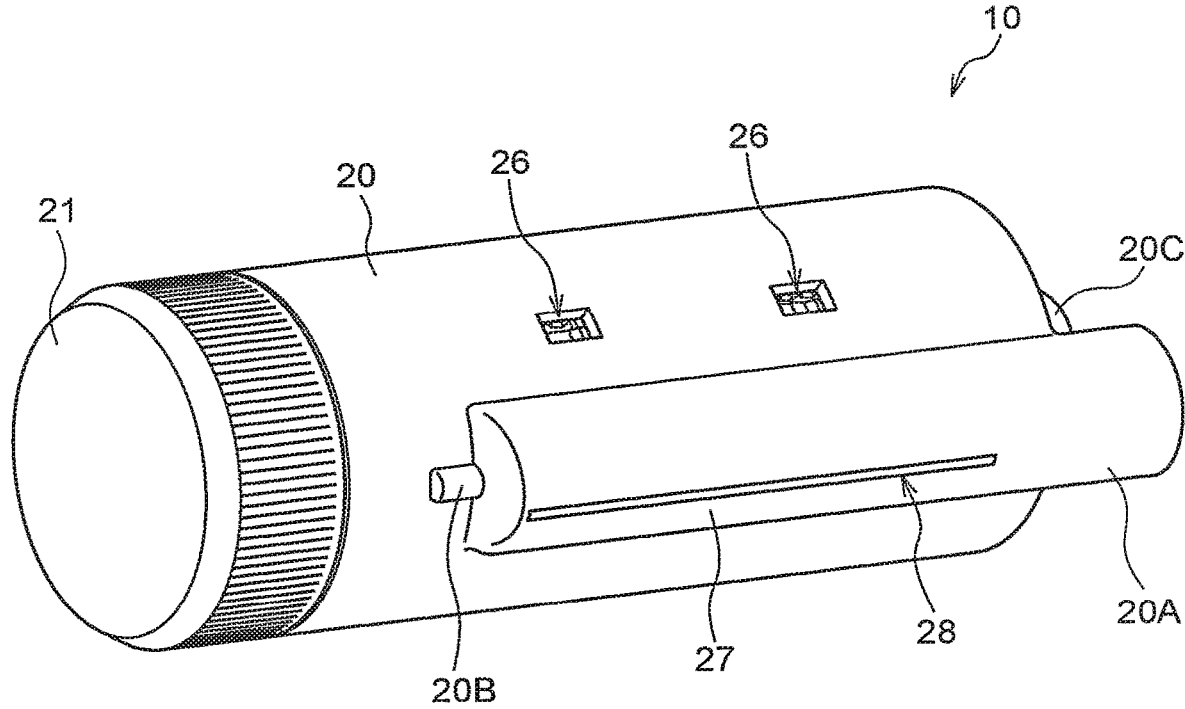
FIG. 2 illustrates the test strip container of FIG. 1 in a front perspective view.
Figure 3:
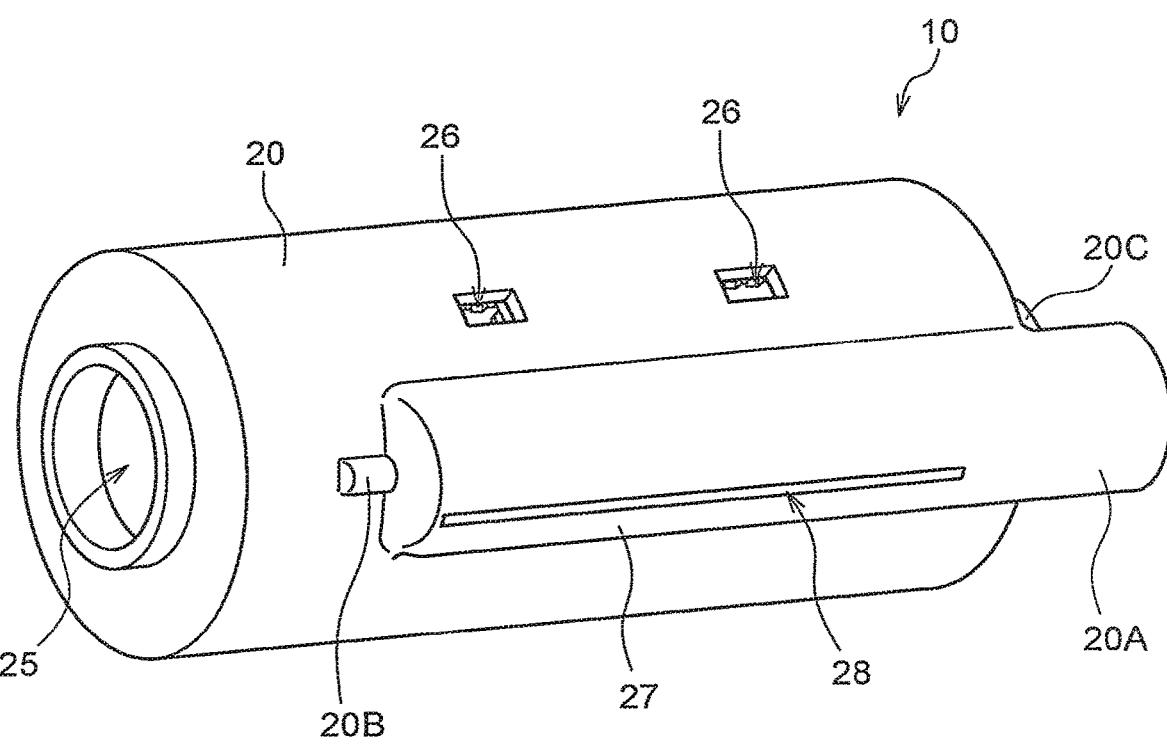
FIG. 3 illustrates, in a front perspective view, a state in which a cap has been removed from the test strip container of FIG. 1.
Figure 4:
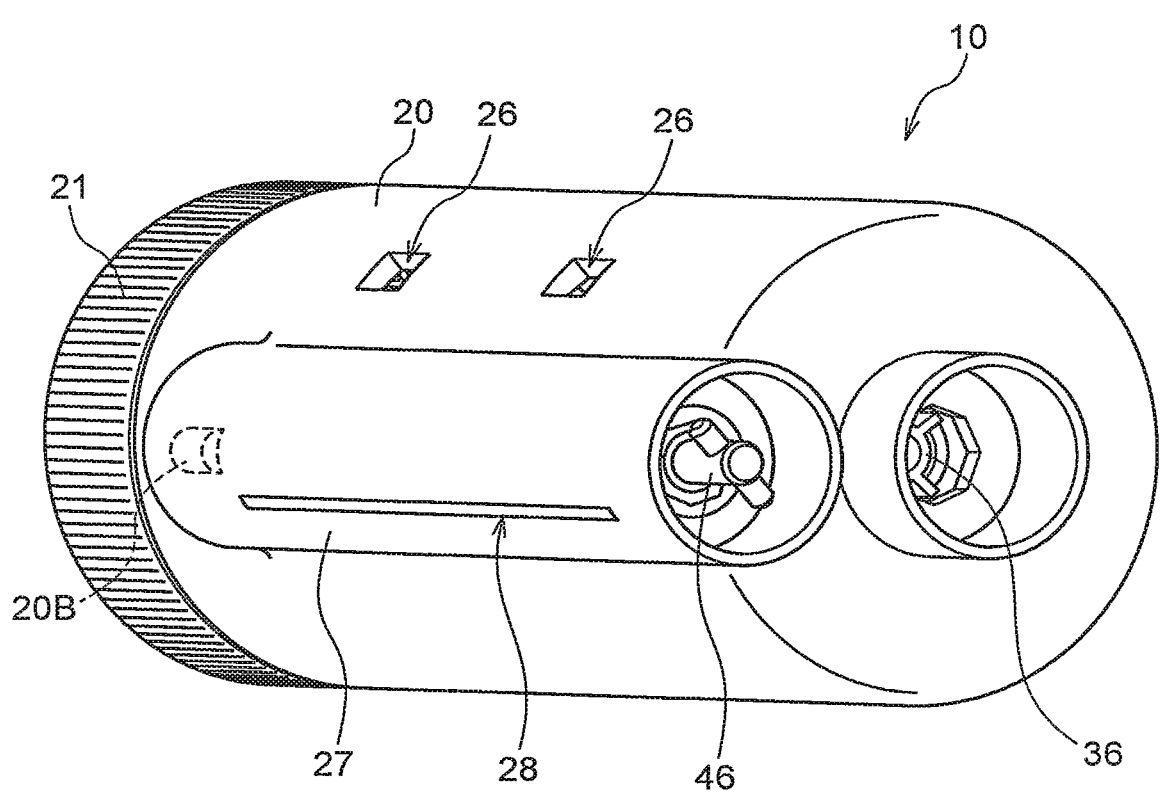
FIG. 4 illustrates the test strip container of FIG. 1 in a rear perspective view.

FIG. 1 illustrates a test strip container 10 of a present exemplary embodiment in a front view. FIG. 2 illustrates the test strip container 10 in a front perspective view. FIG. 3 illustrates, in a front perspective view, a state in which a cap 21 has been removed from the test strip container 10. FIG. 4 illustrates the test strip container 10 in a rear perspective view. Note that, in the following description, the direction in which the cap 21 (FIG. 1, FIG. 2, FIG. 4) is provided at the test strip container 10 is referred to as the front side, and the direction in which a connecting portion 20C is provided at the test strip container 10 is referred to as the rear side.

The test strip container 10 of the present exemplary embodiment has an accommodating member 20 whose side surface is cylindrical and in whose interior test strips 90 (see FIG. 6A to FIG. 6C) are accommodated. Accordingly, the length of the accommodating member 20 in the longitudinal direction is the same as or longer than the length of the test strip 90. As illustrated in FIG. 1, FIG. 2 and FIG. 4, the cap 21 that is shaped as a short cylinder is attached to one end side of the accommodating member 20. A door accommodating portion 27 that is shaped as a cylinder and projects outward is provided at the side surface of the accommodating member 20. The door accommodating portion 27 is a shape in which a portion of a solid cylinder, whose diameter is smaller than the accommodating member 20 and whose length in the longitudinal direction is greater than or equal to the length of the test strip 90, projects outward from the accommodating member 20. Further, a discharge opening 28, which is an opening of the same length or longer than the test strip 90, is provided along the longitudinal direction of the door accommodating portion 27. The discharge opening 28 communicates the interior and the exterior of the door accommodating portion 27 at the lower side of the door accommodating portion 27.

Figure 9:
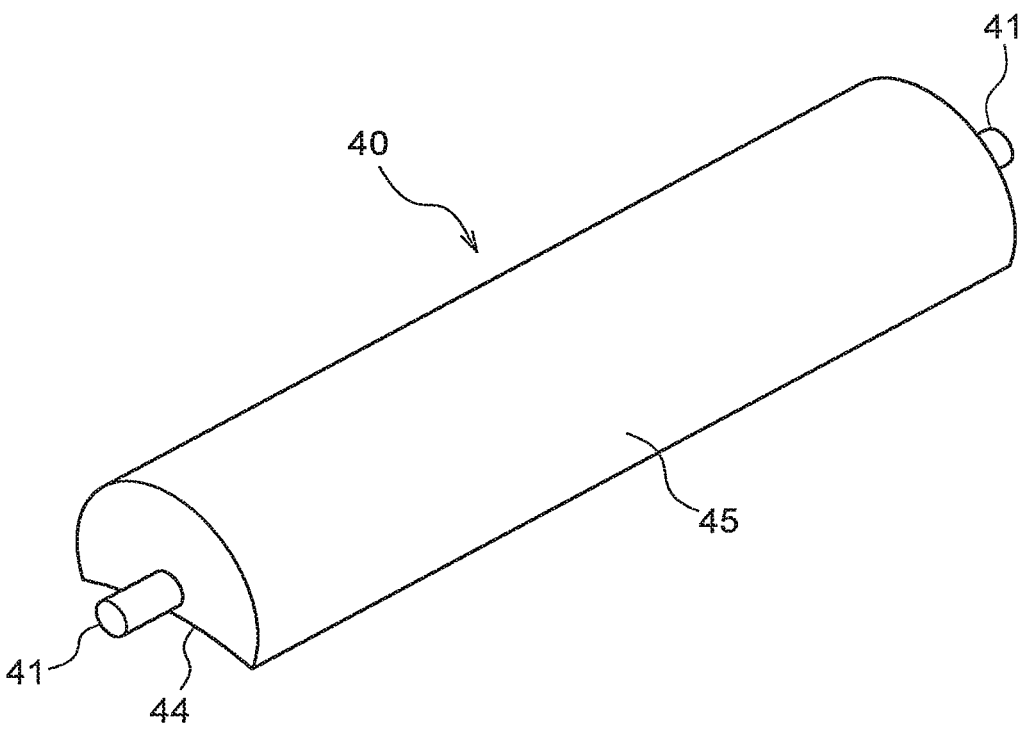
FIG. 9 is an outer perspective view of a door member.
Figure 10:
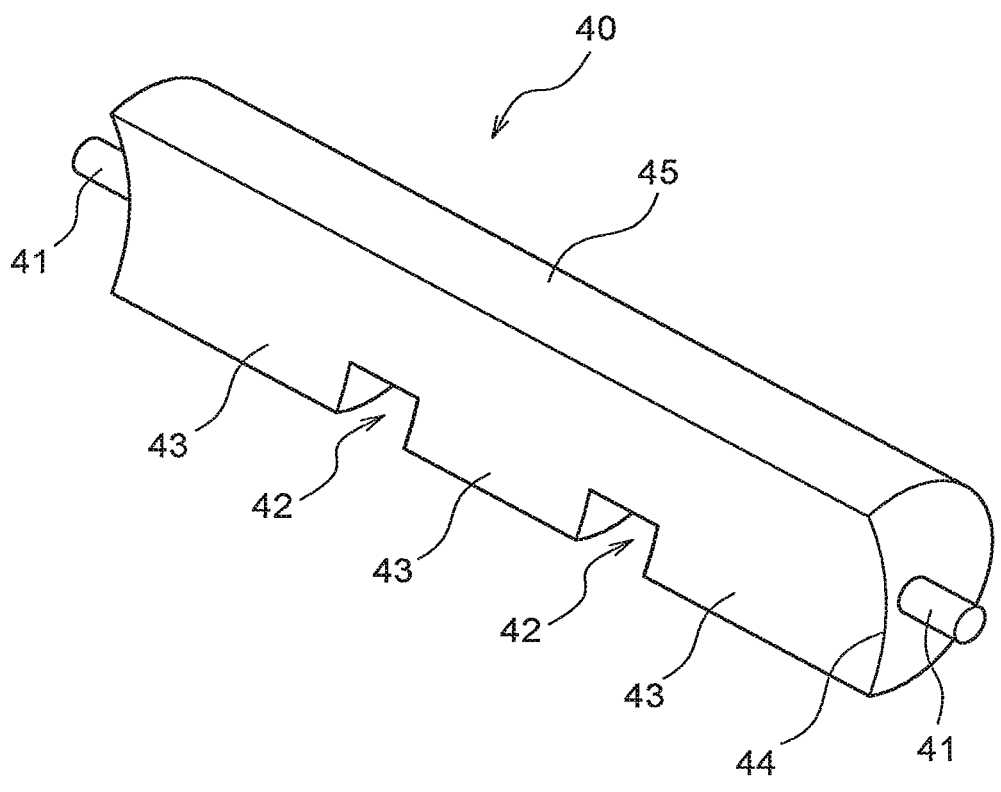
FIG. 10 is an inner perspective view of the door member.

A door member 40, which is the shape illustrated in an outer perspective view in FIG. 9 and in an inner perspective view in FIG. 10, is accommodated in the door accommodating portion 27. The door member 40 has a shape that is substantially crescent-shaped in cross-section, as if a portion of the side surface of a solid cylinder has been hollowed out at the concavely curved surface of a cylindrical surface 22 of the accommodating member 20. The convexly curved surface of this side surface is referred to as a cutting-off portion 45, and the concavely curved surface is referred to as an inclined surface 44. Cut-out portions 42 that are rectangular are formed in two places of the lower edge of the inclined surface 44. This lower edge is divided, by these cut-out portions 42 that are at two places, into three scooping portions 43 that are shaped as tongue pieces. Door shafts 41, which are provided on an axial center of the solid cylinder of the door member 40, project out from the both ends of the door member 40.

The front side of the door accommodating portion 27 is connected to a bearing 20B that is cylindrical and has a smaller diameter than the door accommodating portion 27 and bulges out from the side surface of the accommodating member 20. One of the door shafts 41 is accommodated in this bearing 20B. Further, sensing windows 26 that are rectangular are formed at two places in a vicinity above the door accommodating portion 27. The door member 40 is provided at the side surface of the accommodating member 20 in a direction running along the longitudinal direction of the accommodating member 20.

On the other hand, a driving shaft accommodating portion 20A, which is cylindrical and bulges outward and is connected to the door accommodating portion 27, is provided at the another end side of the accommodating member 20. As illustrated in FIG. 4, a door driving shaft 46 is accommodated in this driving shaft accommodating portion 20A. The door driving shaft 46 and the door shafts 41 have the same axial centers. The door driving shaft 46 is held by an opening/closing operation device 4 (see FIG. 13). Due to the door driving shaft 46 rotating around the axial center, the door member 40 rotates. Moreover, the connecting portion 20C that is cylindrical and has a slightly smaller diameter projects out at the another end side of the accommodating member 20. This connecting portion 20C is connected to a rotation driving device 3 (see FIG. 13) when the test strip container 10 is attached to a test strip discharging mechanism 1. A rotation driving shaft 36 of a rotating member 30 (FIG. 7, FIG. 8) can be seen from an opening provided in the center of the connecting portion 20C.

Figure 5:
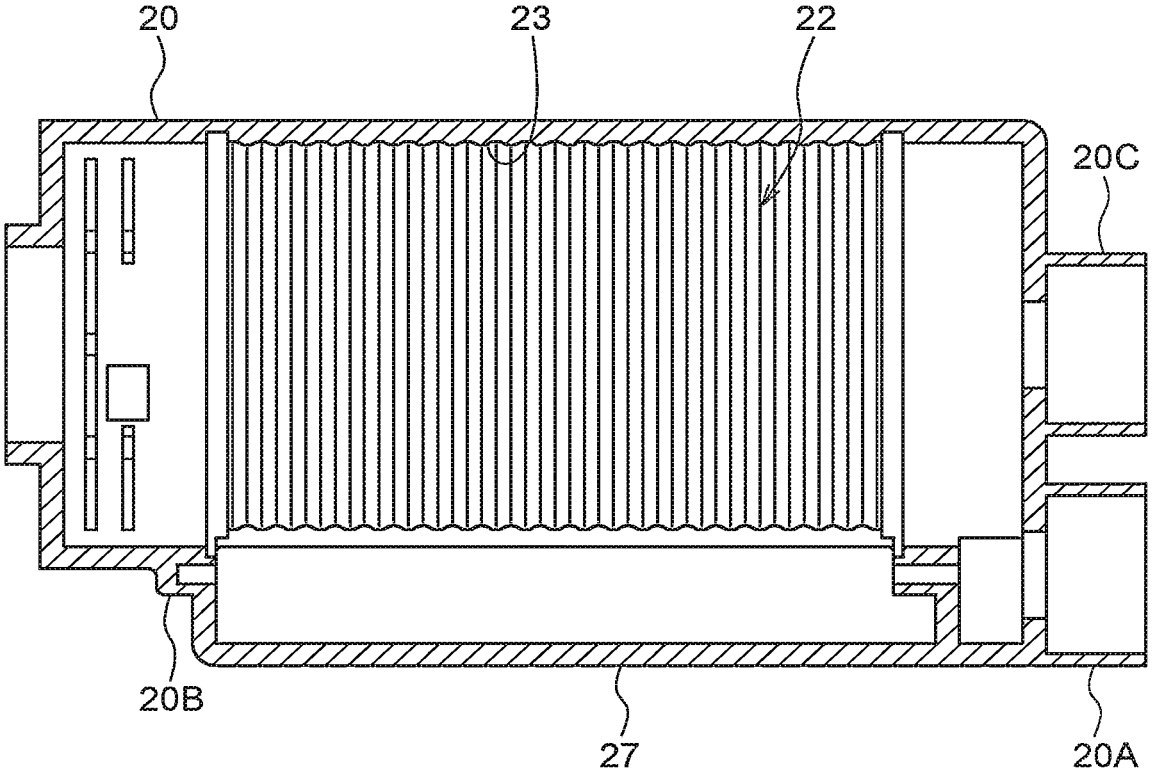
FIG. 5 illustrates, in a cross-section along line D-D' of FIG. 1, a cylindrical surface that is the inner periphery of an accommodating member at the test strip container of FIG. 1.

As illustrated in FIG. 5 that shows the cross-section along line D-D' of FIG. 1, the entire inner periphery of the accommodating member 20 is the cylindrical surface 22 that has a cylindrical shape. Moreover, plural inner peripheral grooves 23 are formed in the cylindrical surface 22 along the peripheral direction. Note that the inner peripheral grooves 23 do not have to be formed in the cylindrical surface 22. The central axis of the cylinder formed by the cylindrical surface 22 is central axis 15 of the accommodating member 20.

Figure 6A:
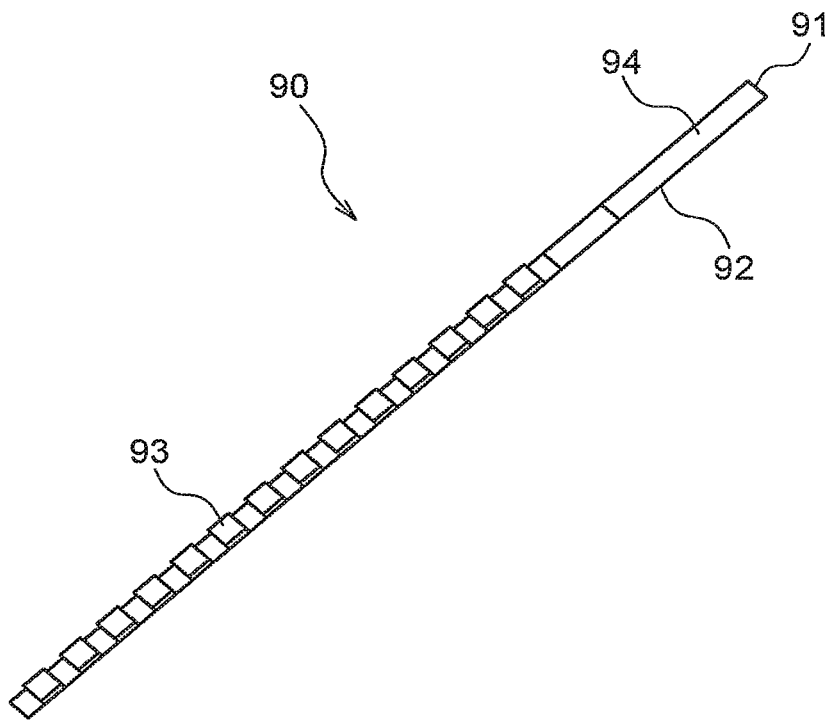
FIG. 6A illustrates a test strip in a perspective view.
Figure 6B:
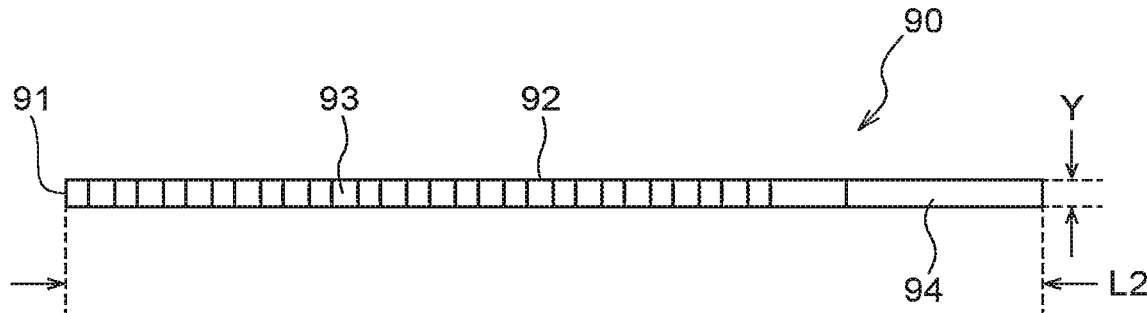
FIG. 6B illustrates the test strip in a front view.
Figure 6C:
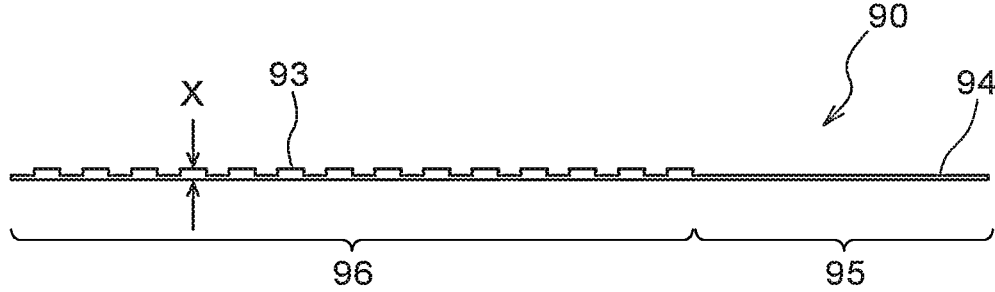
FIG. 6C illustrates the test strip in a side view.

The test strip 90 that is elongated and illustrated in FIG. 6A to FIG. 6C is held at the interior of the accommodating member 20 of the test strip container 10. The test strip 90 in the present exemplary embodiment has the property that the quality thereof easily changes due to the humidity of the outside air or the like. An example is a urine testing paper or a biosensor for blood glucose level measurement, or the like. A reagent that reacts to humidity, i.e., moisture, is used at this test strip. For example, the test strip contains a component that changes color by reacting with moisture, or a component that dissolves due to moisture. Therefore, the test strip container 10 is structured such that outside air does not enter into the interior of the accommodating member 20. A drying agent such as silica gel or the like is placed in the interior of the accommodating member 20 as needed. Namely, even if the amount of outside air that flows in due to temporary opening is small, outside air flows in each time that the test strip 90 is discharged from the accommodating member 20, and therefore, the test strips 90 that stay a long time within the accommodating member 20 deteriorate due to humidity. As described hereinafter, the test strip container 10 of the present exemplary embodiment is structured such that outside air substantially does not enter at all into the accommodating member 20.

In the present exemplary embodiment, a urine test strip for measuring the concentration of or the absence or presence of a physical characteristic or a specific component within urine, is given as an example of the test strip 90. As illustrated, the test strip 90 is a structure in which plural reagent pads 93 are disposed on a strip-shaped substrate 94. A grasping portion 95 that is grasped within an unillustrated measuring device is provided at one end of the substrate 94, and the other region of the substrate 94 is a reagent pad placement region 96 (see FIG. 6C). The plural reagent pads 93 are disposed at the reagent pad placement region 96 in series along the longitudinal direction with a fixed interval therebetween.

The material of the substrate 94 is not particularly limited, and examples thereof are resin, metal, glass and the like. The color of the substrate is not particularly limited, and may be any of white, grey, black, a chromatic color, or transparent. The size of the substrate 94 is not particularly limited, and is determined appropriately in accordance with the items to be tested, the standards of the analyzing device that is used, and the like, and can be, for example, a length of 50~150 mm, a width of 2~10 mm, and a thickness of 0.1~1.0 mm. In the present exemplary embodiment, the length in the long-length direction of the test strip 90, i.e., the length of long side 92, is L2 (FIG. 6B), and the length in the short-length direction, i.e., the length of short side 91, is Y (FIG. 6B). Accordingly, the length of the accommodating member 20 in the longitudinal direction is greater than or equal to the length of the test strip. In this way, the size of the test strip 90 that is suitable for the test strip container 10 of the present exemplary embodiment is limited.

Examples of the material of the reagent pad 93 are filter paper, glass-fiber filter paper, knit fabric, woven fabric, non-woven fabric, a membrane filter, a porous resin sheet, a plastic film, and the like. Further, the shape of the reagent pad 93 is not particularly limited, and is square, rectangular, circular, oval or the like. The size of the reagent pad 93 is not particularly limited, and, when the shape thereof is rectangular, for example, the size can be made to be a length and width of 2~10 mm and a thickness of 0.05~1.0 mm. In the present exemplary embodiment, the thickness of the thick-walled portion is X (FIG. 6C). At the time of forming the reagent pad 93, the reagent pad may be molded into a predetermined shape after the reagent is suffused into the above-described pad material, or the reagent may be suffused after the pad material is molded into a predetermined shape. The suffusing of the reagent can be carried out by, for example, immersing the pad material in a reagent solution and drying the pad material. Further, for example, an adhesive or a tackifier can be used in disposing the reagent pads 93 at the substrate 94. For example, polyurethane, acrylic, vinyl chloride, epoxy, nylon, hot melt, cyanoacrylate, rubber or the like can be used as the adhesive or the tackifier.

Note that thickness X of the test strip 90 is the distance of the thickest portion of the test strip used in the test strip container 10, and, at the above-described test strip 90, is the thickness of the reagent pad 93. If the test strip 90 has a portion that is thicker than the reagent pad 93, the thickness of that place is X.

At the test strip discharging mechanism 1 that is described later, the test strip container 10 is attached such that the direction of the imaginary central axis 15 (FIG. 1) of the accommodating member 20 is the horizontal direction. However, the direction of this central axis 15 is not limited to the horizontal direction, and the test strip 90 may be held provided that the direction is a direction that is inclined with respect to the vertical direction (in other words, is not the vertical direction). Namely, of the angles formed by the direction of the central axis 15 and the vertical direction, the magnitude of the angles that are less than or equal to 90° is greater than 0° and less than or equal to 90°, and preferably greater than or equal to 30° and less than or equal to 90°, and more preferably greater than or equal to 45° and less than or equal to 90°, and even more preferably greater than or equal to 60° and less than or equal to 90°, and most preferably 90°, i.e., the horizontal direction.

As illustrated in FIG. 3 that shows a state in which the cap 21 has been removed from the test strip container 10, an insertion opening 25 for inserting the test strip 90 into the accommodating member 20 is formed in the center of the front side of the accommodating member 20.

Figure 7:
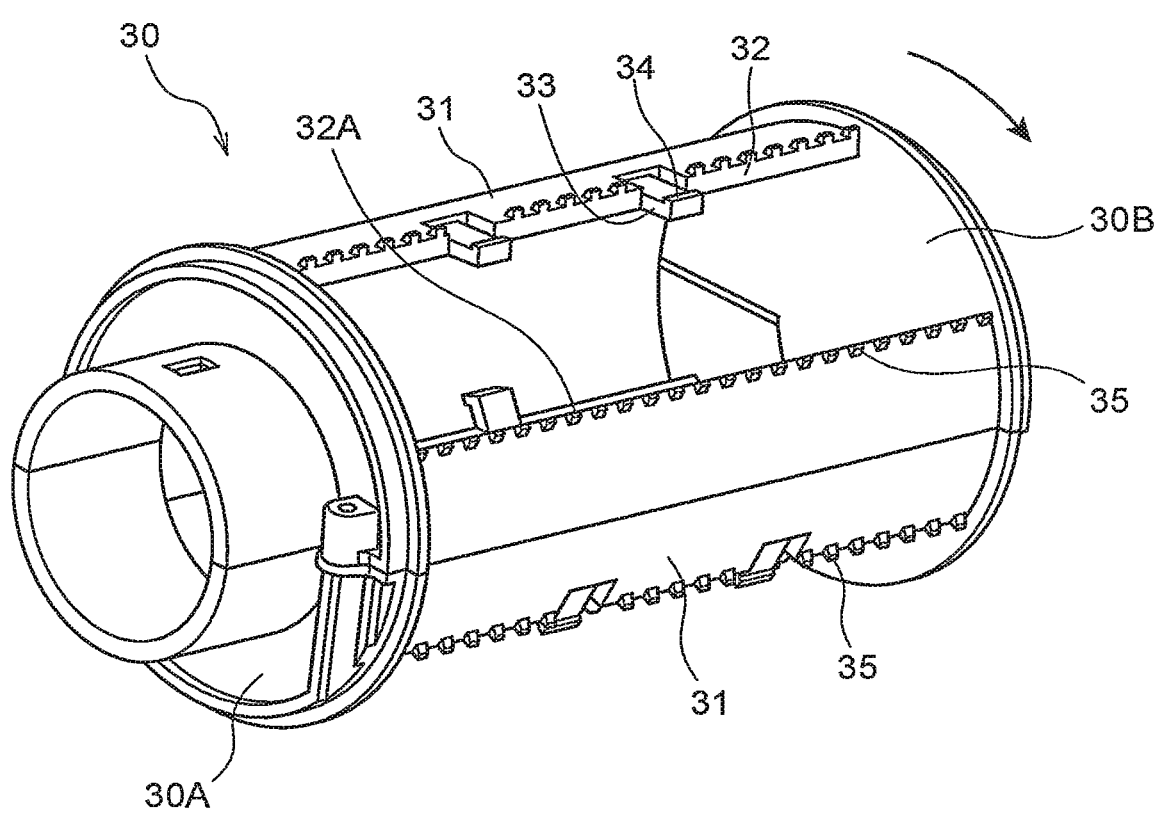
FIG. 7 illustrates, in a front perspective view, a rotating member that is accommodated in the test strip container of FIG. 1.
Figure 8:
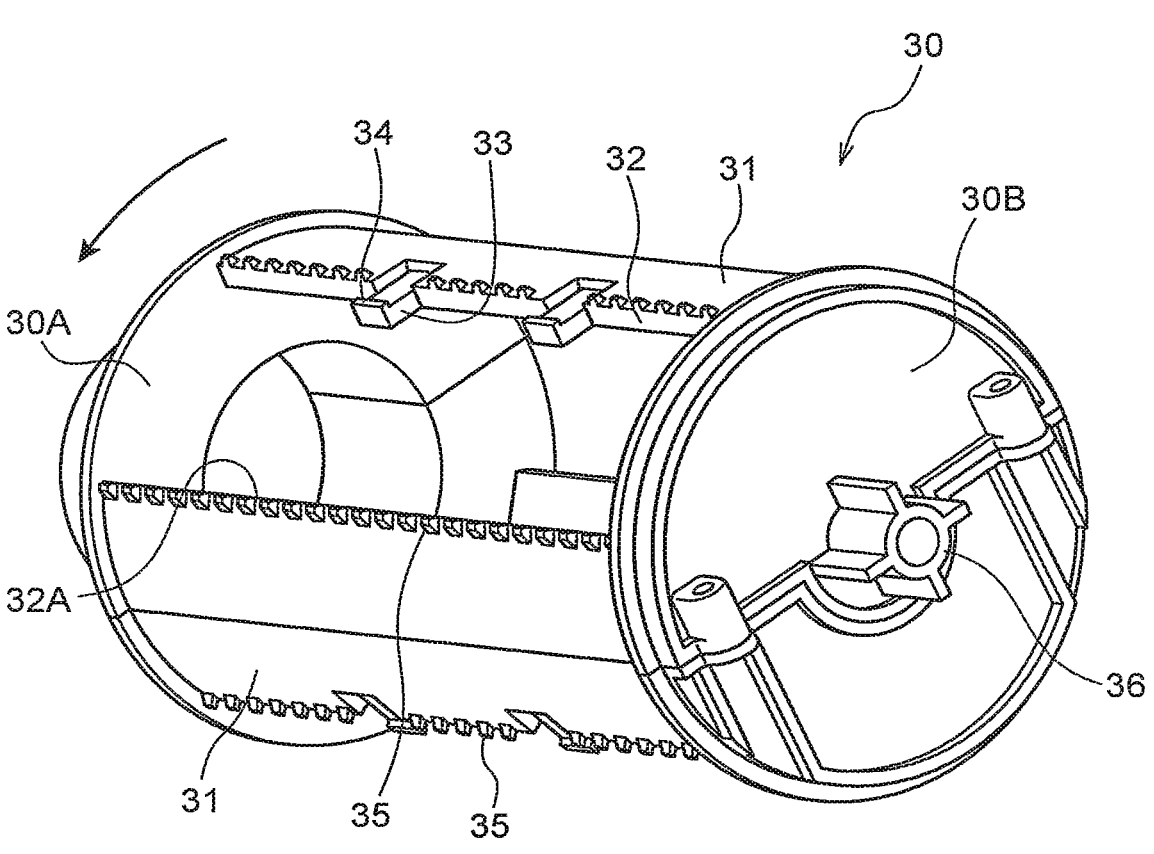
FIG. 8 illustrates the rotating member of FIG. 5 in a rear perspective view.

The rotating member 30 that is accommodated in the accommodating member 20 at the test strip container 10 is illustrated in the front perspective view of FIG. 7 and the rear perspective view of FIG. 8. The rotating member 30 has a front plate 30A that is circular and positioned at the front side, and a rear plate 30B that is circular and is the same diameter as the front plate 30A and is positioned at the rear side so as to be apart from the front plate 30A by a distance that is longer than the length L2 of the long side of the test strip. Moreover, the rotating member 30 has a structure in which plural, and specifically, three, moving members 31 are disposed between the front plate 30A and the rear plate 30B. The moving members 31 are respectively provided so as to be apart by a distance that is longer than length Y of the short side 91 of the test strip. The diameters of the front plate 30A and the rear plate 30B are the same as the diameter of the cylinder formed by the cylindrical surface 22 of the accommodating member 20. The front plate 30A and the rear plate 30B are fixed by the moving members 31 such that the central axis of the circle of the front plate 30A and the central axis of the circle of the rear plate 30B coincide.

In other words, the central axis of the front plate 30A and the central axis of the rear plate 30B coincide, and this is the rotation axis 15 of the rotating member 30. The rotation driving shaft 36 projects out toward the rear side along the central axis of the rear plate 30B from the center of the circle of the rear plate 30B (FIG. 8). When the rotating member 30 is accommodated such that the outer peripheral surface of the front plate 30A and the outer peripheral surface of the rear plate 30B of the rotating member 30 contact the cylindrical surface 22 of the accommodating member 20, the central axis 15 of the accommodating member 20 and the central axis 15 of the rotating member 30 coincide because the diameter of the cylinder formed by the cylindrical surface 22, and the diameter of the front plate 30A and the diameter of the rear plate 30B, are the same.

The rotation driving shaft 36 is connected to the rotation driving device 3 that is described later. Due to rotational force from the rotation driving device 3 being transmitted, the entire rotating member 30 rotates in the direction of the arrows shown in FIG. 7 and FIG. 8. Thereby, the moving members 31 rotate within the accommodating member 20 around the rotation axis 15 that coincides with the central axis 15, and thereby, the test strips 90 are moved at the interior of the accommodating member 20. Namely, the moving members 31 are formed as bodies separate from the accommodating member 20, and rotate with respect to the accommodating member 20. In other words, the moving members 31 rotate around the central axis 15 of the accommodating member 20 while maintaining a predetermined distance from the central axis 15.

A circular opening is provided in the front plate 30A at the center of the circle of the front plate 30A (FIG. 8), and a cylinder of the same outer diameter as this opening is fit therein (FIG. 7). The cylinder projects out forward from the front plate 30A. When the rotating member 30 is accommodated in the accommodating member 20, the cylinder is connected to the insertion opening 25 of the accommodating member 20. Accordingly, the test strip 90 that is inserted in the insertion opening 25 of the test strip container 10 is held between the front plate 30A and the rear plate 30B.

The moving members 31 are members that are substantially plate-shaped and are provided along the direction of the rotation axis 15. The moving members 31 are mounted between the circular surface at the inner side of the front plate 30A and the circular surface at the inner side of rear plate 30B, so as to be apart from the rotation axis 15. The moving member 31 has an outer peripheral surface that faces in the direction of the outer side of the rotating member 30, an inner peripheral surface that faces in the direction of the rotation axis 15, a first side surface that is parallel to the central axis 15 and faces in the rotating direction, and a second side surface that is parallel to the central axis 15 and faces in the direction of the side opposite the rotating direction. The inner peripheral surface and the outer peripheral surface are curved surfaces whose centers are the rotation axis 15. The first side surface and the second side surface are surfaces connecting the outer peripheral surface and the inner peripheral surface, and are flat surfaces that expand from the outer peripheral surface in the direction toward the central axis. Plural sliding projections 35 are disposed at the outer peripheral surface, along the edge between the outer peripheral surface and the first side surface. The sliding projections 35 are projections that fit into the inner peripheral grooves 23 provided at the cylindrical surface 22, at the time when the rotating member 30 is accommodated in the accommodating member 20. The sliding projections 35 shaped as truncated cones whose bottom surfaces are square and that become pointed toward the outer side of the rotating member 30. The surfaces at the rotating direction sides of the sliding projections 35 are flat surfaces that expand toward the rotation axis 15, and form portions of the first side surface of the moving member 31. The first side surface, which includes the rotating direction side surfaces of the sliding projections 35, is a distal end edge 32 of the moving member 31.

Each of the moving members 31 has the distal end edge 32 that corresponds to the distal end portion in the rotating direction and is parallel to the central axis. Two pushing pieces 33, which are rectangular parallelepiped and have predetermined lengths in the longitudinal direction, project out in parallel in the rotating direction from the distal end edge 32 by a predetermined distance D (see FIG. 12) that is longer than at least distance B. The number of the pushing pieces 33 is not limited to two. It suffices for the pushing pieces 33 to be able to hold the test strip 90 even during rotation, and the number thereof may be one or may be three or more. Further, the positions of the pushing pieces 33 in the longitudinal direction are not particularly limited, provided that they can hold the test strip 90 even during rotation. Moreover, a sorting piece 34 that is rectangular parallelepiped projects out from the distal end of the pushing piece toward the outer side, i.e., toward the cylindrical surface 22 (FIG. 5). The plural sliding projections 35 are disposed at the outer peripheral surface of the moving member 31 in rows along the distal end edge 32 and a rear end edge 32A respectively, toward the cylindrical surface 22 (FIG. 5). The sliding projections 35 provided at the outer peripheral surface of the moving member 31, and the inner peripheral grooves 23 (FIG. 5) provided at the cylindrical surface 22 of the accommodating member 20, are formed as a structure of projections and indentations that mesh with each other. The pushing pieces 33 and the sorting pieces 34 are both fixed to the moving member 31 that rotates around the central axis 15 of the accommodating member 20 while maintaining a predetermined distance from the central axis 15. Therefore, the pushing pieces 33 and the sorting pieces 34 also rotate around the central axis 15 while maintaining a predetermined distance from the central axis 15.

Figure 11:
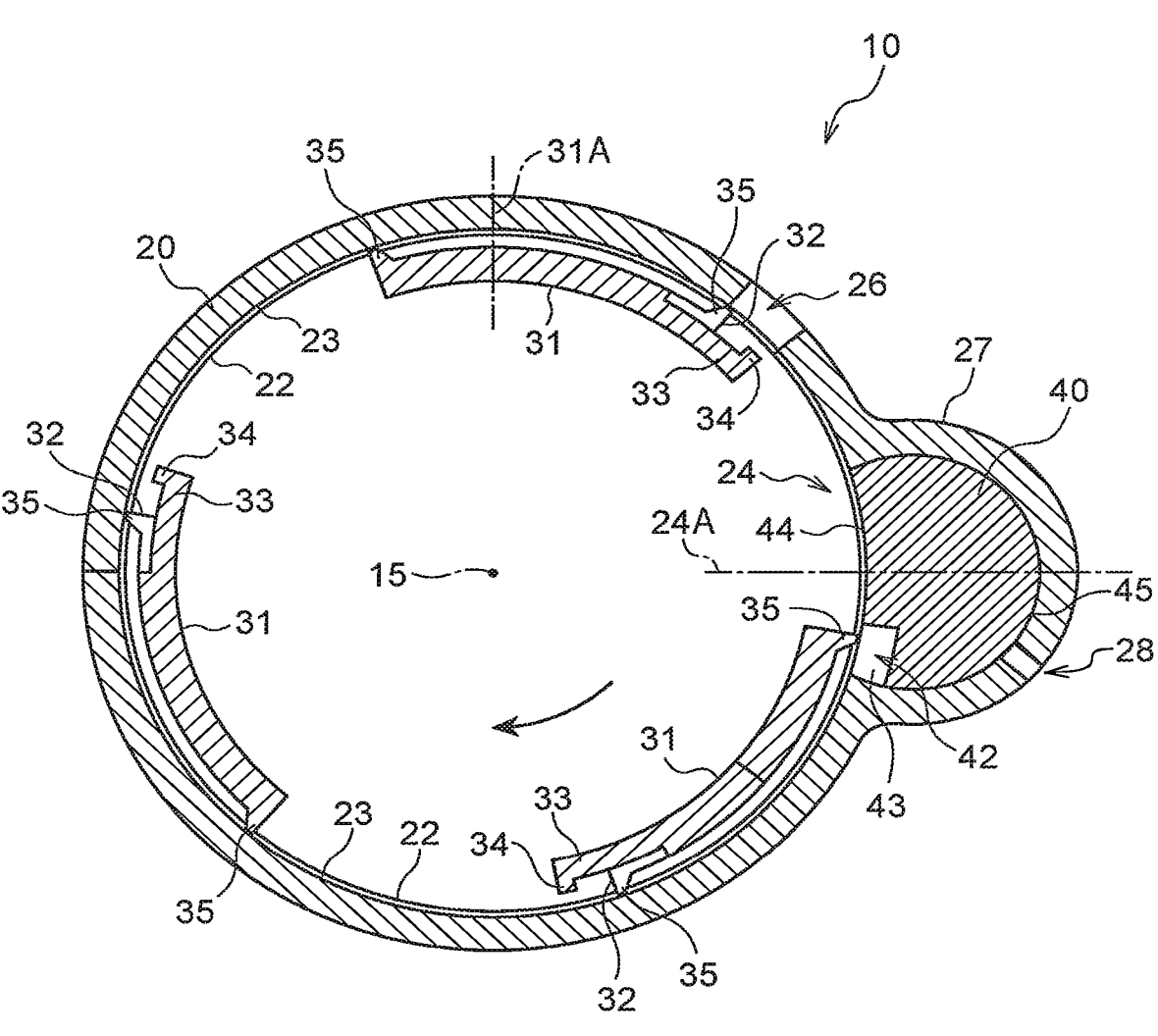
FIG. 11 is a cross-sectional view along line C-C' of FIG. 1.

FIG. 11 is a cross-sectional view along line C-C' of FIG. 1. The cylindrical surface 22 of the accommodating member 20 has a cross-section that is a substantially circular cross-section, and the inner peripheral surface of the door member 40, which is provided at an opening portion 24 that communicates the accommodating member 20 and the door accommodating portion 27, is a circular arc shape that is flush with the cylindrical surface 22 of the accommodating member 20. Further, the three moving members 31 have cross-sectional shapes that are approximately circular arc shaped, and are disposed uniformly with respect to the central axis 15. Note that the moving members 31 do not absolutely have to be disposed uniformly, and the number thereof is not limited to three. However, the number of the test strips 90 that can be held in one round of the rotating member 30 increases in accordance with the number of the moving members 31, and it is preferable that plural moving members 31 be provided in order to improve the speed of taking out the test strips 90 from the test strip container 10. On the other hand, the greater the number of moving members 31, the narrower the interval between the front and rear moving members 31, and the higher the probability of rotation without being able to hold the test strips 90. Therefore, the number of moving members 31 is preferably three to five. Moreover, the sliding projections 35 that are provided at both the distal end side and the rear end side of the moving member 31 fit in the inner peripheral grooves 23 of the cylindrical surface 22, and slide along the inner peripheral grooves 23 in the rotating direction that is shown by the arrows in the drawings. Note that, provided that two or more of the sliding projections 35 are provided, the test strip 90 becoming bitten-in between the moving member 31 and the cylindrical surface 22 can be inhibited even if the sliding projections 35 and the inner peripheral grooves 23 are not meshing together as indentations and projections.

Note that central line 24A that is shown by a dashed line in the drawings is an imaginary line that bisects the opening portion 24 along the longitudinal direction. Here, the central line 24A is at a position that is at the lower side in the rotation direction, with respect to an uppermost position 31A that the moving member 31 at the interior of the accommodating member 20 reaches. Assuming that the rotational angle of this uppermost position 31A is 0°, the central line 24A is preferably at a position of a rotational angle of greater than or equal to 45° and less than or equal to 90°, and more preferably is at the position of 90°.

The moving members 31 rotate and move the test strips 90, which are accommodated in the accommodating member 20, along the cylindrical surface 22 that is the inner peripheral surface of the accommodating member 20. The door member 40 is provided at the side surface of the accommodating member 20 so as to be able to open and close, in order to discharge the test strip 90 to the exterior of the accommodating member 20. When closed, the door member 40 cuts the interior and the exterior of the accommodating member 20 off from each other. The door accommodating portion 27 covers the door member 40 from the outer side of the accommodating member 20. The door member 40 can open and close by rotating at the interior of the door accommodating portion 27.

The discharge opening 28 is provided in order to discharge, to the exterior of the door accommodating portion 27 (i.e., the exterior of the test strip container 10), the test strip 90 that has been discharged to the exterior of the accommodating member 20, i.e., into the door accommodating portion 27. The discharge opening 28 can be opened and closed with respect to the exterior by the door member 40 that rotates within the door accommodating portion 27. Namely, when the discharge opening 28 is closed, the interior and the exterior of the door accommodating portion 27 are cut off from each other. On the other hand, when the discharge opening 28 is open, the door member 40 closes the opening portion 24 of the accommodating member 20 as will be described later. Namely, the test strip container 10 of the present exemplary embodiment is structured such that the discharge opening 28 can be opened in the state in which the accommodating member 20 is closed by the door member 40. For example, such a structure is made possible by a locking mechanism of a physical structure or an electric locking mechanism that, in a case in which the accommodating member 20 is opened by the door member 40, locks the discharge opening 28, and, in a case in which accommodating member 20 is closed by the door member 40, releases the locking and enables opening of the discharge opening 28.

The inclined surface 44 of the door member 40 is the inner peripheral surface that is shaped as a concave surface and is flush with the cylindrical surface 22 that is the inner side surface of the accommodating member 20, at the time when the door member 40 is closed as illustrated in FIG. 11. The cutting-off portion 45 that is at the side opposite the inclined surface 44 is shaped as a cylindrical, convex surface that corresponds to the cylindrical, concave surface of the interior of the door accommodating portion 27. At the time when the door member 40 is closed as illustrated in FIG. 11, the cutting-off portion 45 closes both the opening portion 24 and the discharge opening 28. On the other hand, at the time when the discharge opening 28 is open as described later, the cutting-off portion 45 cuts the interior of the accommodating member 20 off from the exterior.

Figure 12:
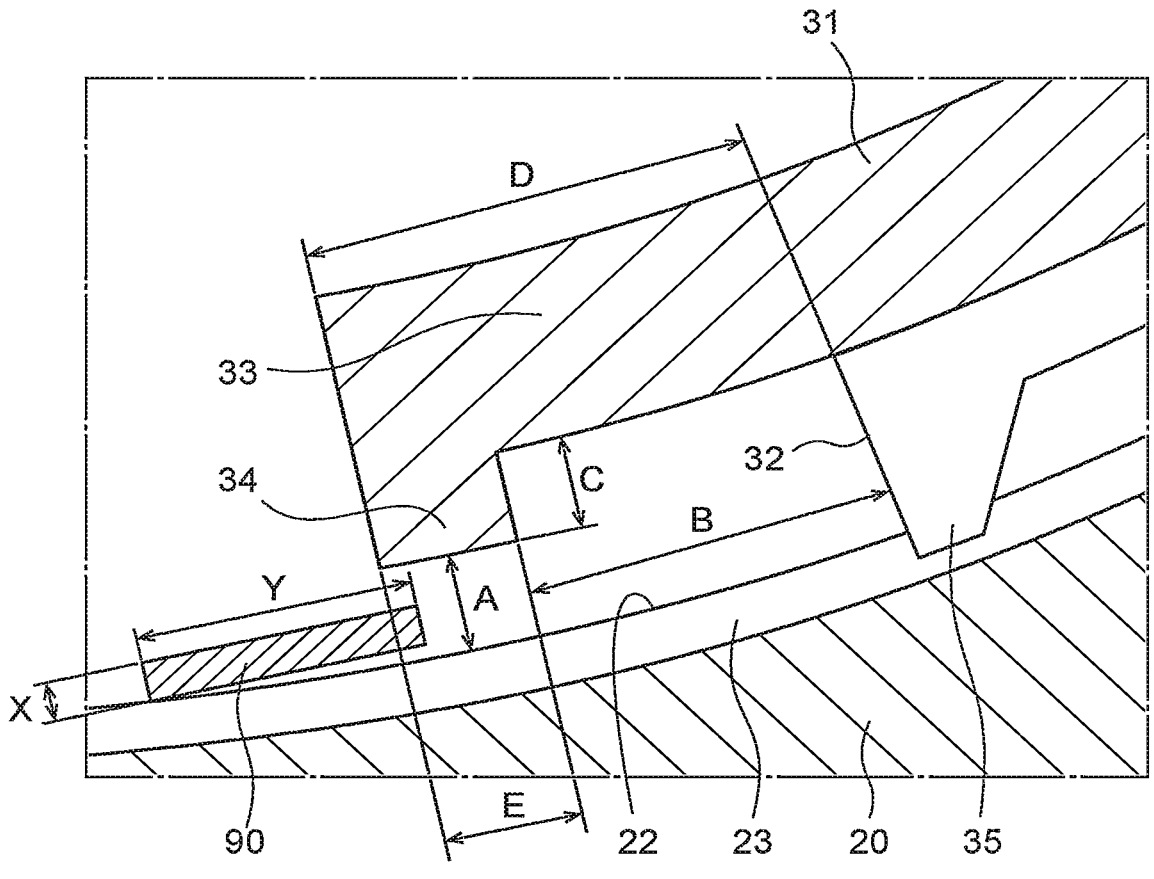
FIG. 12 illustrates a pushing piece and a sorting piece in an enlarged manner.

The positional relationships between the cylindrical surface 22 and the pushing piece 33 and the sorting piece 34 of the moving member 31 are shown in the enlarged sectional view of FIG. 12. Namely, the distance between the cylindrical surface 22 and the position nearest to the cylindrical surface 22 at the distal end edge 32 of the moving member 31 (i.e., the distal end of the sliding projection 35) is set to be less than the thickness X of the test strip 90 (FIG. 6C). Thereby, the test strip 90 becoming bitten-in between the moving member 31 and the cylindrical surface 22 is inhibited, and the distal end edge 32 can push the test strip 90 in the rotating direction as the moving member 31 rotates. Further, distance A between the cylindrical surface 22 and the position of the sorting piece 34 that is nearest to the cylindrical surface 22 is set to be greater than or equal to the thickness X of the test strip 90 and less than two times X.

Namely, the distance A is a distance such that one of the test strips 90 can enter in between the sorting pieces 34 and the cylindrical surface 22, but two or more of the test strips cannot enter in. Thereby, two or more of the test strips 90 overlapping and simultaneously entering in between the pushing pieces 33 and the cylindrical surface 22 is inhibited. Note that, from the standpoints of tolerating errors in manufacturing of the test strips 90 and ease of entry of the test strips 90, the distance A is preferably greater than or equal to 1.1 times the thickness X of the test strip 90, and more preferably greater than or equal to 1.2 times. Further, because the reagent pad 93 at the test strip 90 such as that described above is formed of a material such as filter paper or the like, there are cases in which, due to the reagent pad 93 being pressed, the thickness X becomes thinner than X. Accordingly, the distance A is preferably less than 1.8 times the thickness X of the test strip 90, and more preferably less than 1.6 times.

Further, the distance B from the distal end edge 32 of the moving member 31 to the sorting piece 34, with respect to the length Y (FIG. 6B) in the short-length direction of the test strip 90, is set to be greater than or equal to Y and less than two times Y. Namely, the distance B is a distance that is such that one of the test strips 90 can enter-in in the rotating direction between the cylindrical surface 22 and the pushing pieces 33 that are disposed between the distal end edge 32 and the sorting pieces 34, but two or more of the test strips 90 cannot enter-in. Thereby, two or more of the test strips 90 being held so as to be lined up in the rotating direction between the pushing pieces 33 and the cylindrical surface 22 is inhibited. Note that, from the standpoints of tolerating errors in manufacturing of the test strips 90 and ease of entry of the test strips 90, the distance B is preferably greater than or equal to 1.1 times the length Y of the test strip 90, and more preferably greater than or equal to 1.2 times. Further, there is the concern that two or more of the test strips will enter in if the test strips 90 stand up. Therefore, the distance B is preferably less than 1.8 times the length Y of the test strip 90, and more preferably less than 1.6 times.

Moreover, length C of the portion which projects out from the pushing piece 33 toward the cylindrical surface 22 at the sorting piece 34 is set to be greater than or equal to 0.5 times the thickness X of the test strip 90, and less than 1.5 times X. Namely, the length C is a distance that is such that the one test strip 90 that has entered in between the cylindrical surface 22 and the pushing pieces 33 disposed between the distal end edge 32 and the sorting pieces 34 can be held, but two or more of the test strips 90 cannot be held. Due to these conditions of the distance B and the length C, even if the moving member 31 (the pushing pieces 33) rotates while holding two or more of the test strips 90, immediately after the pushing pieces 33 reach the uppermost position 31A (i.e., when the pushing pieces 33 reach the position at which the vertically-downward vector is small), only the test strip 90 that is at the pushing pieces 33 side from the moving member 31 is held at the inner sides of the projecting portions of length C of the sorting pieces 34, and the test strips 90 other than that cannot be held by the sorting pieces 34, and therefore, fall down. Note that length C being greater than or equal to 0.5 times the thickness X of the test strip 90 and less than 1.0 times X is more preferable from the standpoint that the test strips that are other than the one test strip 90 that is held do not at all contact the inner sides of the projecting portions of length C of the sorting pieces 34, and therefore, can reliably be made to drop down.

Further, distance E (see FIG. 12), which is the length of the sorting piece 34 in the rotating direction, with respect to the length Y of the test strip 90 in the short-length direction, is set to be less than Y, and preferably is less than 0.5 times the length Y of the test strip 90. Due to this condition of the distance E, the test strip that is held between the sorting pieces 34 and the cylindrical surface 22 can fall down immediately after the uppermost position 31A is reached. Note that the distance E is substantially the same length as the distance obtained by subtracting the distance B from the distance D.

Figure 13:
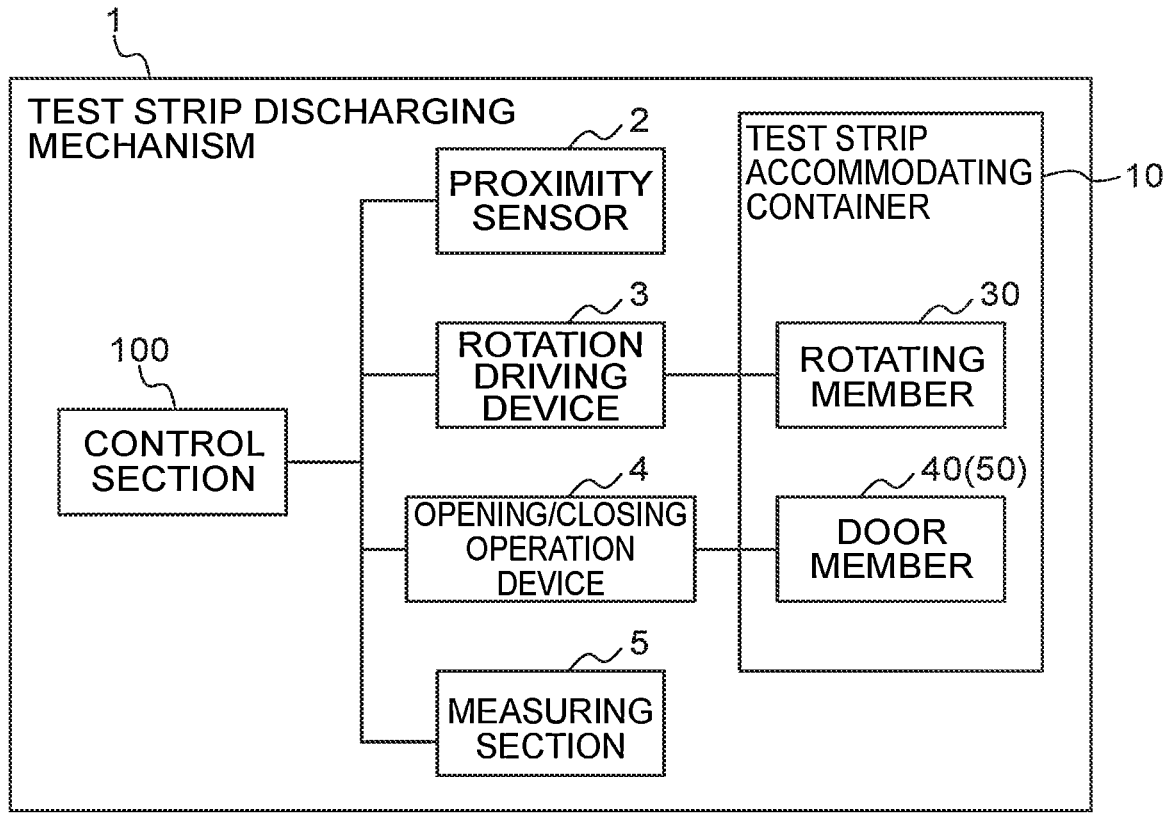
FIG. 13 is a functional block drawing of a test strip holding mechanism.

A functional block drawing of the test strip discharging mechanism 1 is illustrated in FIG. 13. The test strip discharging mechanism 1 is structured as a measuring apparatus that measures, by the test strip 90 to which a specific reagent has been applied, the concentration of or the absence or presence of a physical characteristic or a specific component of a biological specimen such as, for example, a urine sample.

A control section 100 is electrically connected to the test strip discharging mechanism 1, and controls the respective sections thereof. The control section 100 controls a proximity sensor 2, the rotation driving device 3, the opening/closing operation device 4, and a measuring section 5 by hardware structures described later. When the test strip container 10 is attached to the test strip discharging mechanism 1, as described above, the rotation driving device 3 is connected to the rotation driving shaft 36 (FIG. 8) of the rotating member 30, and further, the opening/closing operation device 4 is connected to the door driving shaft 46 (FIG. 4) of the door member 40. The proximity sensor 2 is structured by, for example, an optical sensor or a proximity sensor or the like, and, through the sensing windows 26 (FIG. 11) of the accommodating member 20, senses the approach of the moving member 31 to the door member 40. Note that the proximity sensor 2 may sense the approach of the test strip 90 that is held at the moving member 31. In accordance with the sensing by the proximity sensor 2, the control section 100 drives the rotation driving device 3, and rotates or stops the rotating member 30 (the moving members 31). Further, in accordance with the sensing by the proximity sensor 2, the control section 100 drives the opening/closing operation device 4, and opens or closes the door member 40. Further, the control section 100 also controls the measuring section 5 that serves as a measuring apparatus and is structured by various portions and devices.

Figure 14:
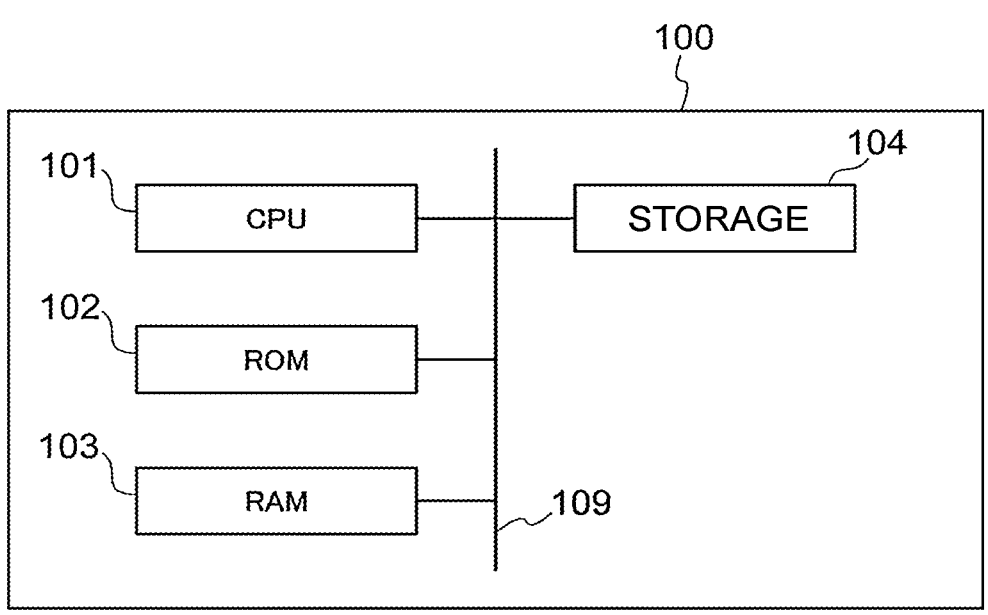
FIG. 14 is a block drawing illustrating hardware structures of a control section of FIG. 13.

As illustrated by the hardware structures in FIG. 14, the control section 100 has a CPU (Central Processing Unit) 101, a ROM (Read Only Memory) 102, a RAM (Random Access Memory) 103, and a storage 104. These respective structures are connected so as to be able to communicate with one another via bus 109.

The CPU 101 is a central computing processing unit, and executes various programs and controls respective sections. Namely, the CPU 101 reads-out a program from the ROM 102 or the storage 104, and executes the program by using the RAM 103 as a workspace. The CPU 101 carries out control of the above-described respective structures, and various computing processings, in accordance with programs recorded in the ROM 102 or the storage 104.

The ROM 102 stores various programs and various data. The RAM 103 temporarily stores programs and data as a workspace. The storage 104 is structured by an HDD (Hard Disk Drive), an SSD (Solid State Drive) or a flash memory, and stores various programs, including the operating system, and various data. In the present aspect, programs and various data relating to measurements and judgments are stored in the ROM 102 or the storage 104. Further, measured data also can be stored in the storage 104.

The control section 100 executes control of the proximity sensor 2, the rotation driving device 3, the opening/closing operation device 4 and the measuring section 5 due to, among the above-described hardware structures, the CPU 101 executing the above-described programs.

Due to the above-described structure, by control of the control section 100, when the proximity sensor 2 senses the approach of the moving member 31 to the door member 40, the rotation driving device 3 can stop the rotation of the moving member 31, and the opening/closing operation device 4 can close the discharge opening 28 while opening the door member 40. Further, the control section 100 can also carry out control so as to open the discharge opening 28 at the time when the door member 40 is closed. Moreover, the control section 100 can also carry out control so as to restart movement of the moving member 31 after closing the door member 40 again. The control section 100 can also carry out control such that this operation of the opening/closing operation device 4 is carried out due to the proximity sensor 2 sensing the approach of the moving member 31. Moreover, the control section 100 can control the stopping of rotation by the rotation driving device 3 due to the proximity sensor 2 sensing the approach of the moving member 31, and can control the restarting of rotation by the rotation driving device 3 when the opening/closing operation device 4 closes the opening portion 24.

Figure 15A:
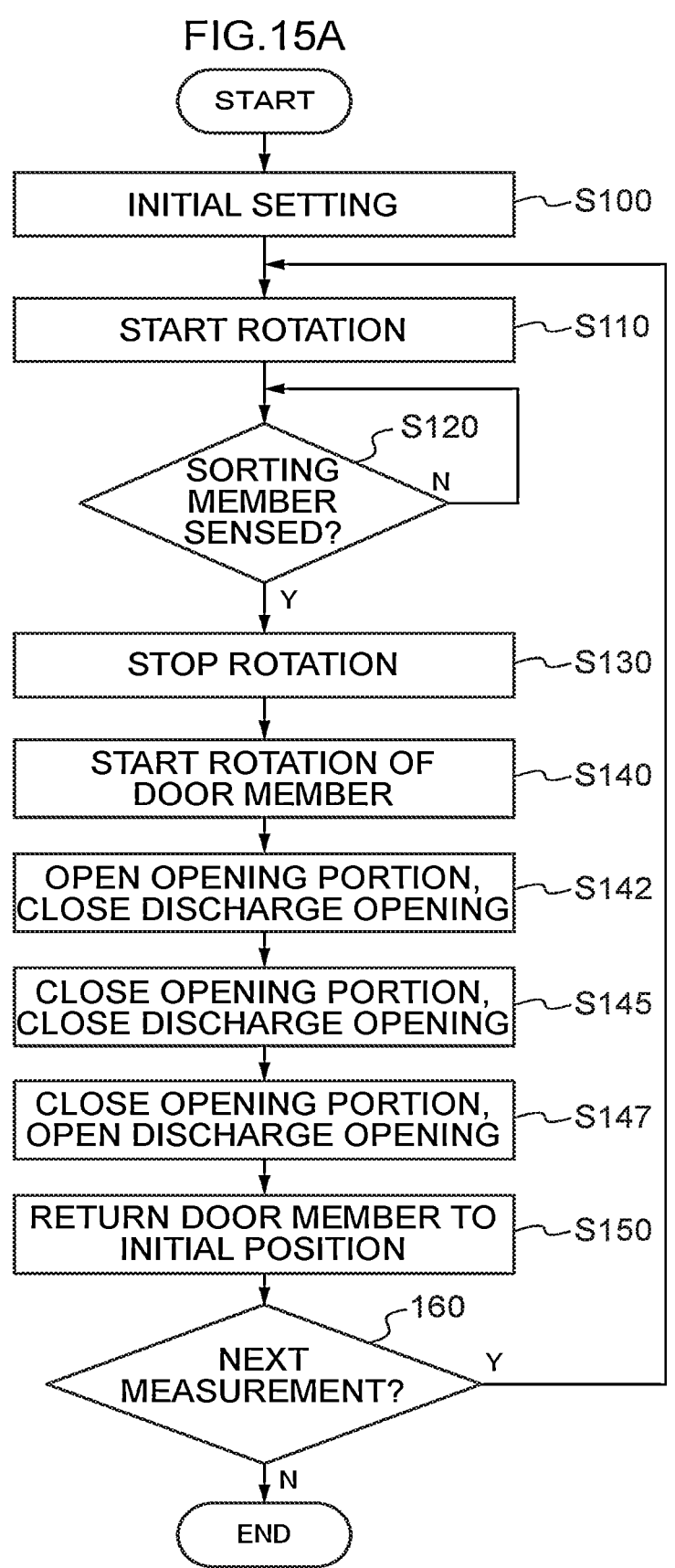
FIG. 15A is a flowchart illustrating an overview of test strip discharging processing.
Figure 15B:
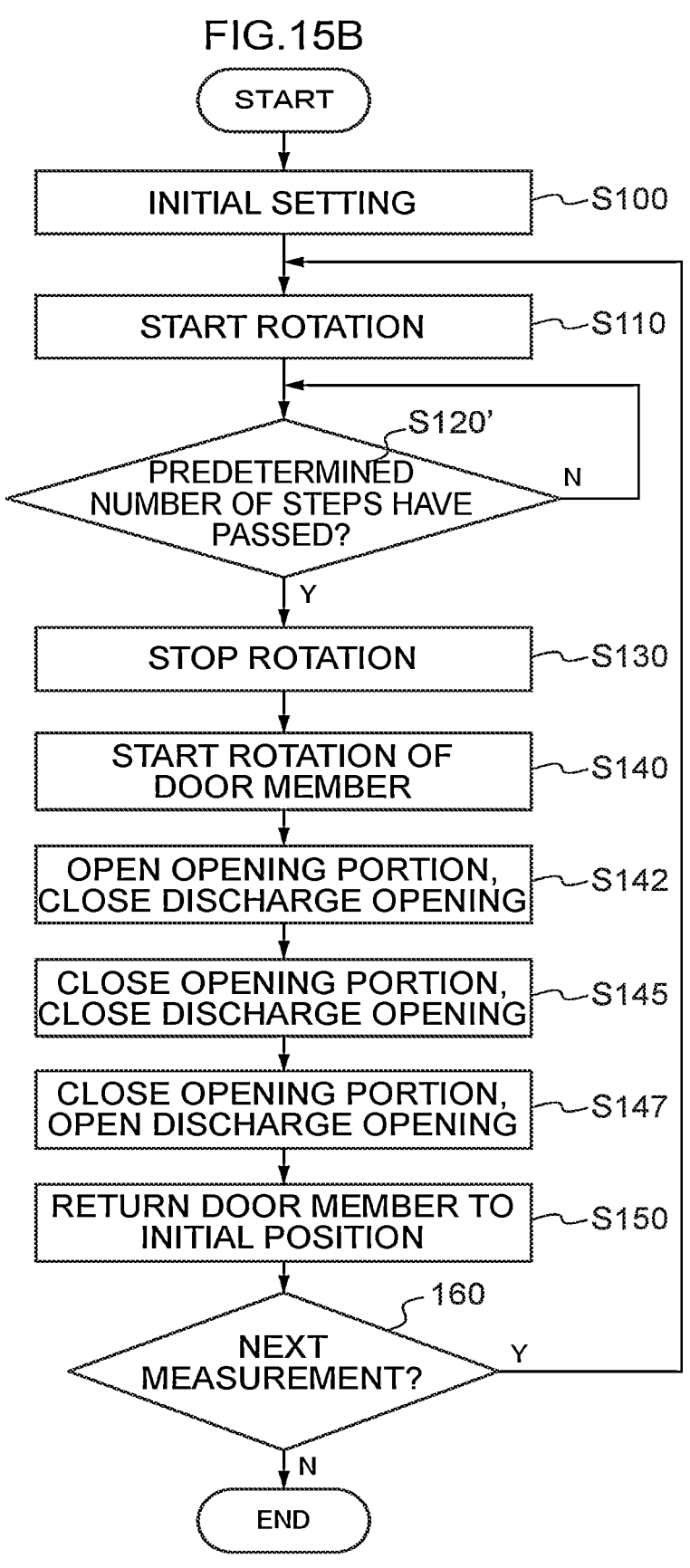
FIG. 15B is a flowchart illustrating an overview of test strip discharging processing.

The taking-out of the test strip 90 by the test strip container 10 of the present exemplary embodiment is described next with reference to the flowchart of FIG. 15A (or FIG. 15B) and the cross-sectional views of FIG. 16A to FIG. 16G. Note that the cross-sectional views of FIG. 16A to FIG. 16G explain operation focusing on one of the moving members 31, but, of course, operations at the other two moving members 31 also are executed concurrently.

First, when the power of the test strip discharging mechanism 1 is turned on, initial setting of the devices is executed in the step shown in S100. This initial setting also includes setting the rotating member 30 at its initial position of rotation due to the control section 100 controlling the rotation driving device 3.

Then, after preparations for measurement have been completed, in the step shown in S110, the control section 100 drives the rotation driving device 3 and starts rotation of the rotating member 30. In the step shown in S120, the control section 100 continues the rotation of the rotating member 30 until the proximity sensor 2 senses the moving member 31 through the sensing windows 26. Note that, in the case of a structure that does not have the proximity sensor 2 and that employs, for example, a step motor as the rotation driving device 3, in the step shown in S120' in the flowchart of FIG. 15B, the control section 100 can continue the rotation of the rotating member 30 until a predetermined number of steps have passed (e.g., the number of steps needed until the next moving member 31 approaches the opening portion 24 after stoppage of rotation and restarting of rotation).

Figure 16A:
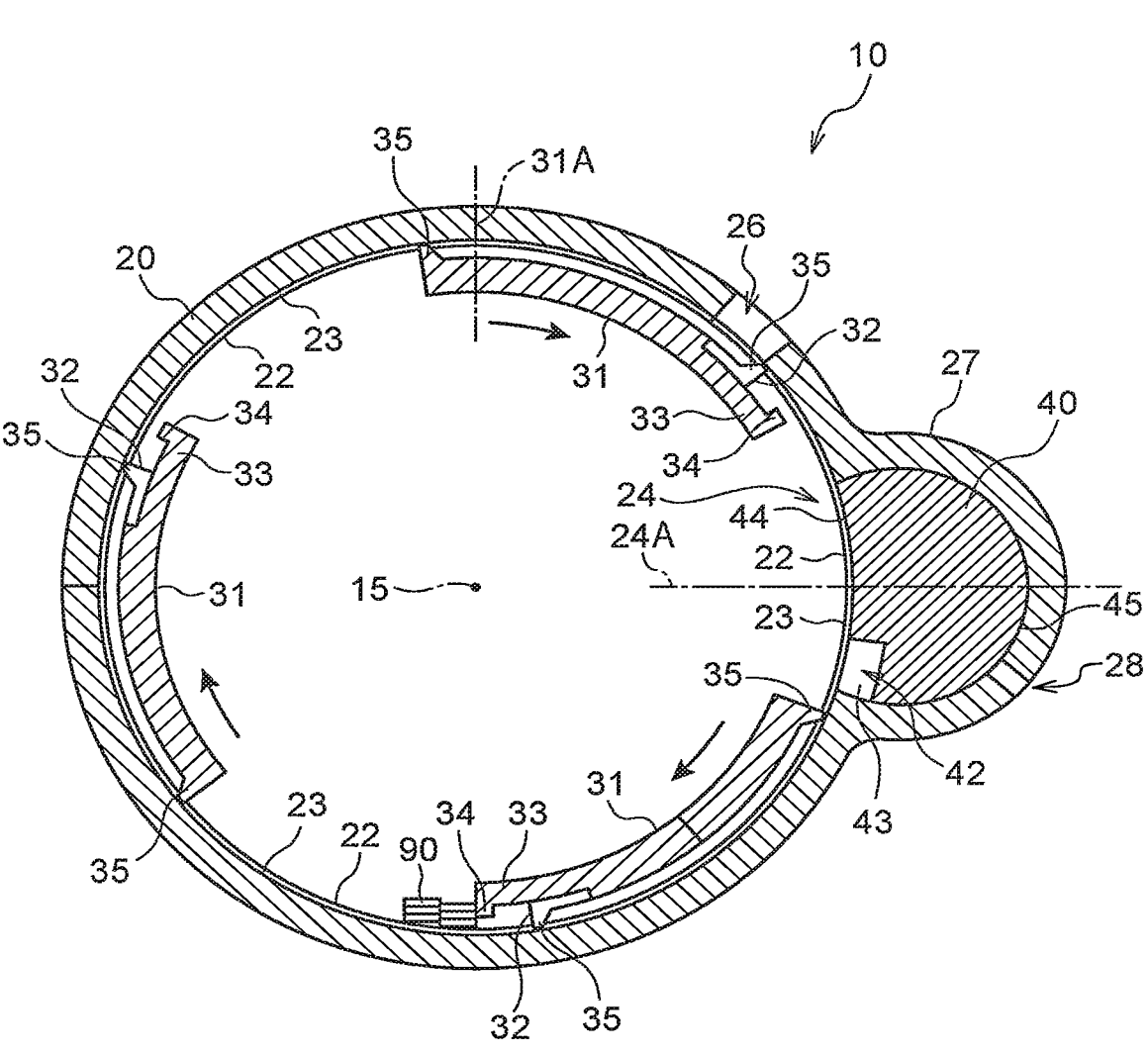
FIG. 16A illustrates a state of holding the test strip, in a cross-sectional view.

During this time, in FIG. 16A, the plural test strips 90 stay at the lower portion of the interior space of the accommodating member 20. The pushing pieces 33 of the moving member 31 push, in the rotating direction, these plural test strips 90 that are staying there. On the other hand, the door member 40 that is in the closed state closes the opening portion 24 by the inclined surface 44, and closes the discharge opening 28 by the cutting-off portion 45.

Figure 16B:
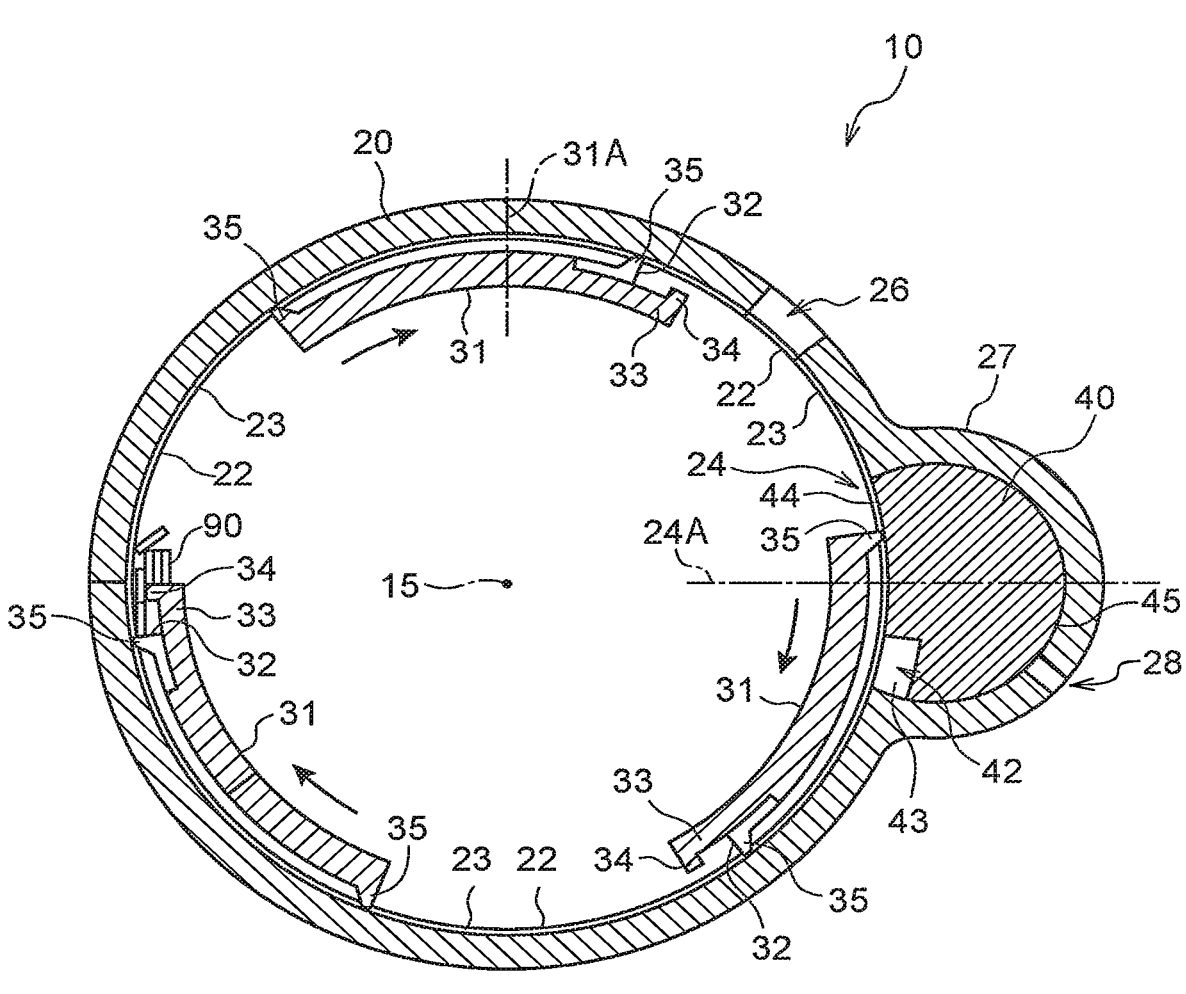
FIG. 16B illustrates a state of holding the test strip, in a cross-sectional view.

When the moving member 31 continues moving by rotating at the interior of the accommodating member 20 while holding the test strips 90 and comes to a position past the lowermost position in the vertical direction as illustrated in FIG. 16B, only one of the test strips 90 that were positioned at the outermost side slips through the gap of width A (see FIG. 12) that is between the sorting pieces 34 and the cylindrical surface 22, and enters in to a position at which the long side 92 thereof is made to contact the distal end edge 32. Note that there are cases in which only a portion of another test strip 90 as well enters into the gap between the sorting pieces 34 and the cylindrical surface 22. The other test strip 90 is raised up by the pushing pieces 33.

Figure 16C:
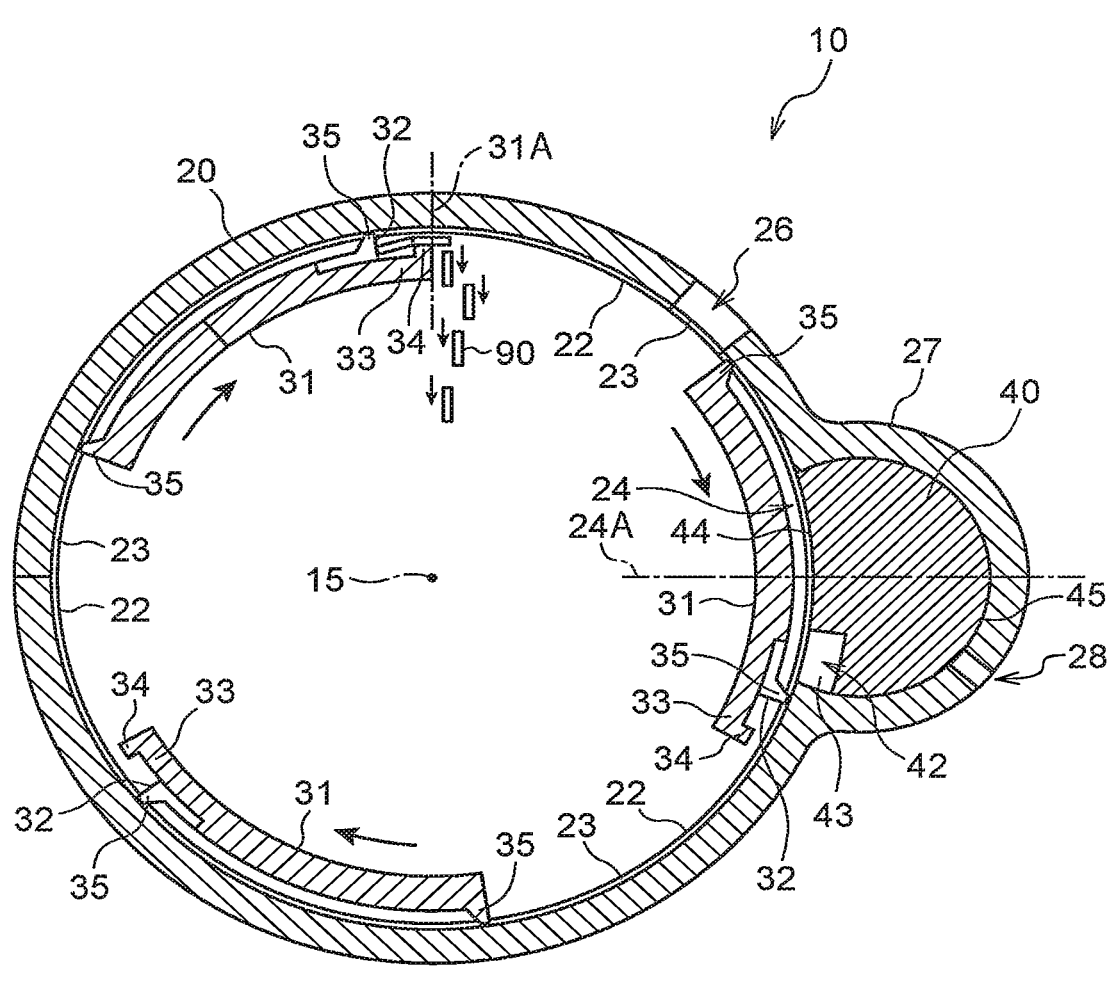
FIG. 16C illustrates a state of holding the test strip, in a cross-sectional view.
Figure 16D:
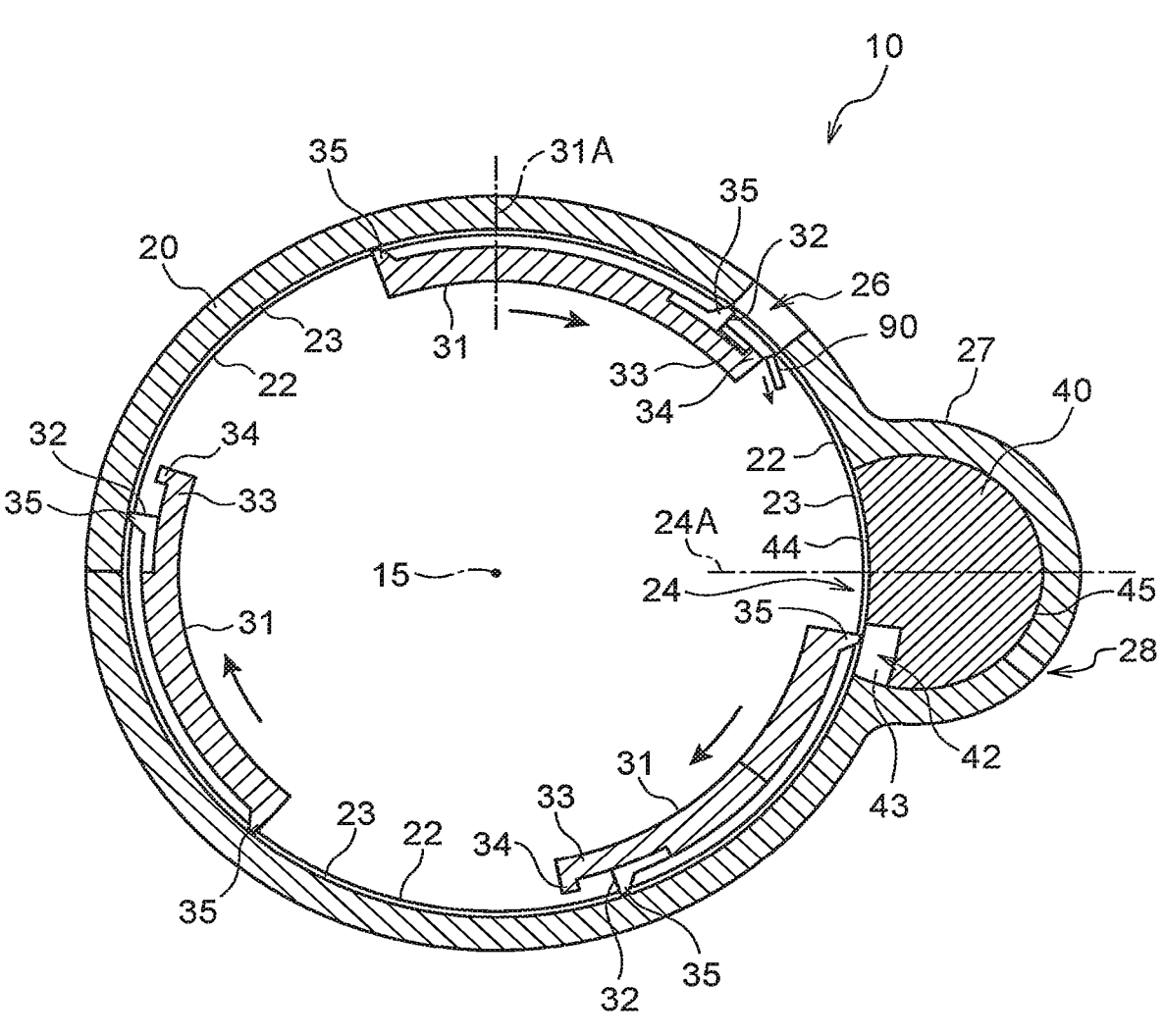
FIG. 16D illustrates a state of holding the test strip, in a cross-sectional view.

When the moving member 31 continues to rotate further, and the pushing pieces 33 reach the uppermost position 31A as illustrated in FIG. 16C, all of the test strips 90 that could not enter into the gap between the sorting pieces 34 and the cylindrical surface 22 fall downward. Then, when the moving member 31 rotates further to the position shown in FIG. 16D, the test strip 90, at which only a portion thereof entered into the gap between the sorting pieces 34 and the cylindrical surface 22, also falls down ultimately, but the test strip 90, which entered in up to the point of contacting the distal end edge 32, is held up by the pushing pieces 33 and the sorting pieces 34 and avoids falling down.

Namely, due to the distance A between the cylindrical surface 22 and the nearest position of the sorting piece 34 to the cylindrical surface 22 being X≤A≤2X, only one of the test strips 90 is held at a position that is rotated slightly from the uppermost position 31A due to the moving member 31 rotating. Note that, due to the distance B from the distal end edge 32 of the pushing piece 33 to the sorting piece 34 being Y<B<2Y, and the length C of the portion of the sorting piece 34 that projects out from the pushing piece 33 toward the cylindrical surface 22 being 0.5X<C<1.5X, the moving member 31 can be set in a state of even more reliably holding only the test strip 90 at a position that is rotated slightly from the uppermost position 31A.

Figure 16E:
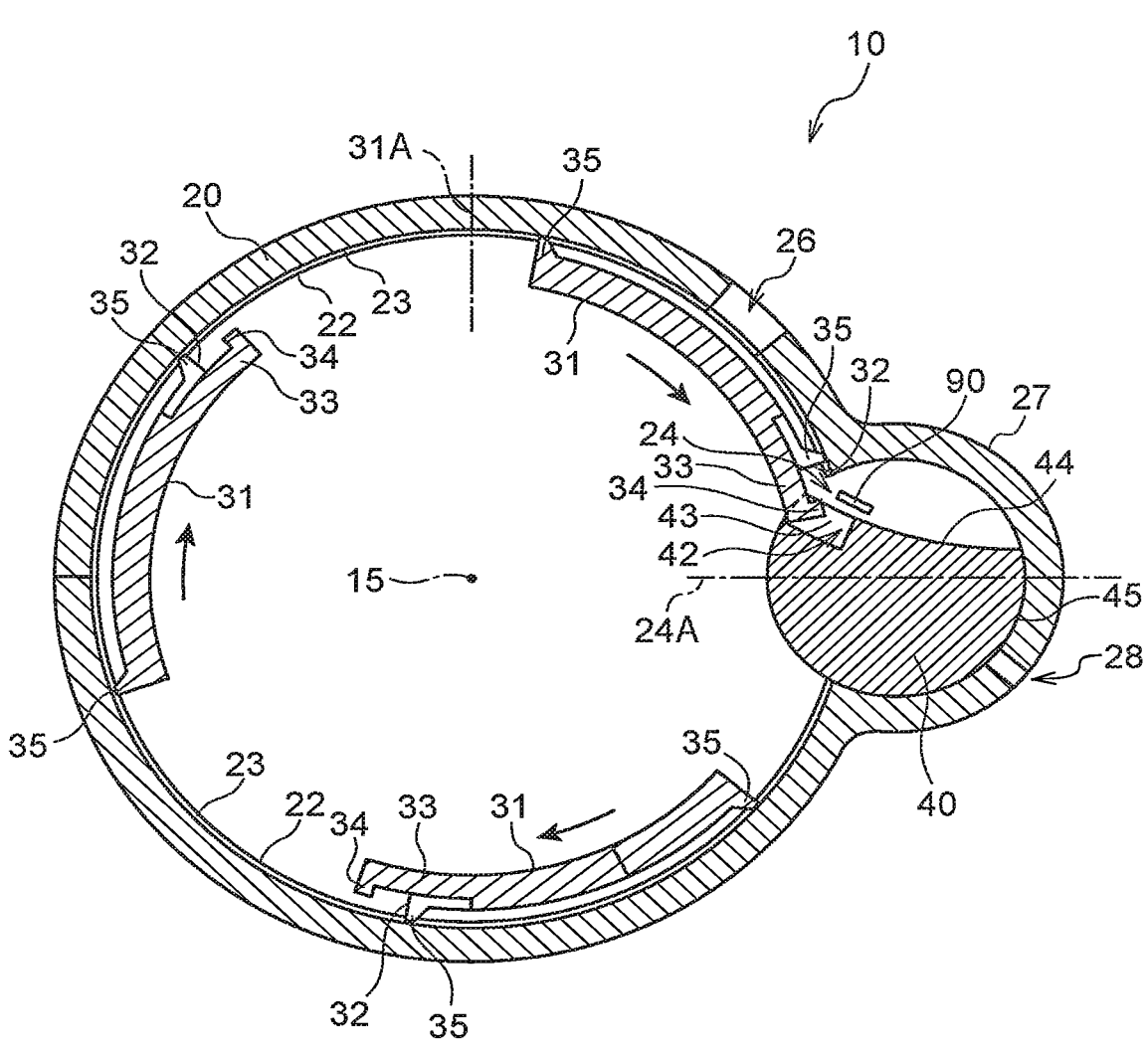
FIG. 16E illustrates a state in which the test strip is discharged, in a cross-sectional view.

Further, when the moving member 31 rotates to the position illustrated in FIG. 16E, in the step shown in S120, the proximity sensor 2 senses the approach of the moving member 31 (or, in the step shown in S120', the control section 100 senses passage of the predetermined number of steps), and, in the step shown in S130, the control section 100 stops driving of the rotation driving device 3, and rotation of the moving member 31 stops. Then, in the next step shown in S140, the control section 100 drives the opening/closing operation device 4, and rotates the door member 40 to the state illustrated in FIG. 16E and opens the door member 40.

Namely, due to this rotation of the door member 40, simultaneously with the cut-out portions 42 reaching the positions of the pushing pieces 33, the inclined surface 44 of the scooping portions 43 applies impact to the test strip 90 that was held by the pushing pieces 33 and the sorting pieces 34, and the test strip 90 is discharged to the outer side of the accommodating member 20. At this time, the inclined surface 44 may be made to collide with the pushing pieces 33 or the test strip 90. At this time, the test strip 90 that has been discharged and dropped down is led by the inclined surface 44 of the door member 40 to the exterior of the accommodating member 20. In this state, the door member 40 closes the discharge opening 28 while opening the accommodating member 20.

Figure 16F:
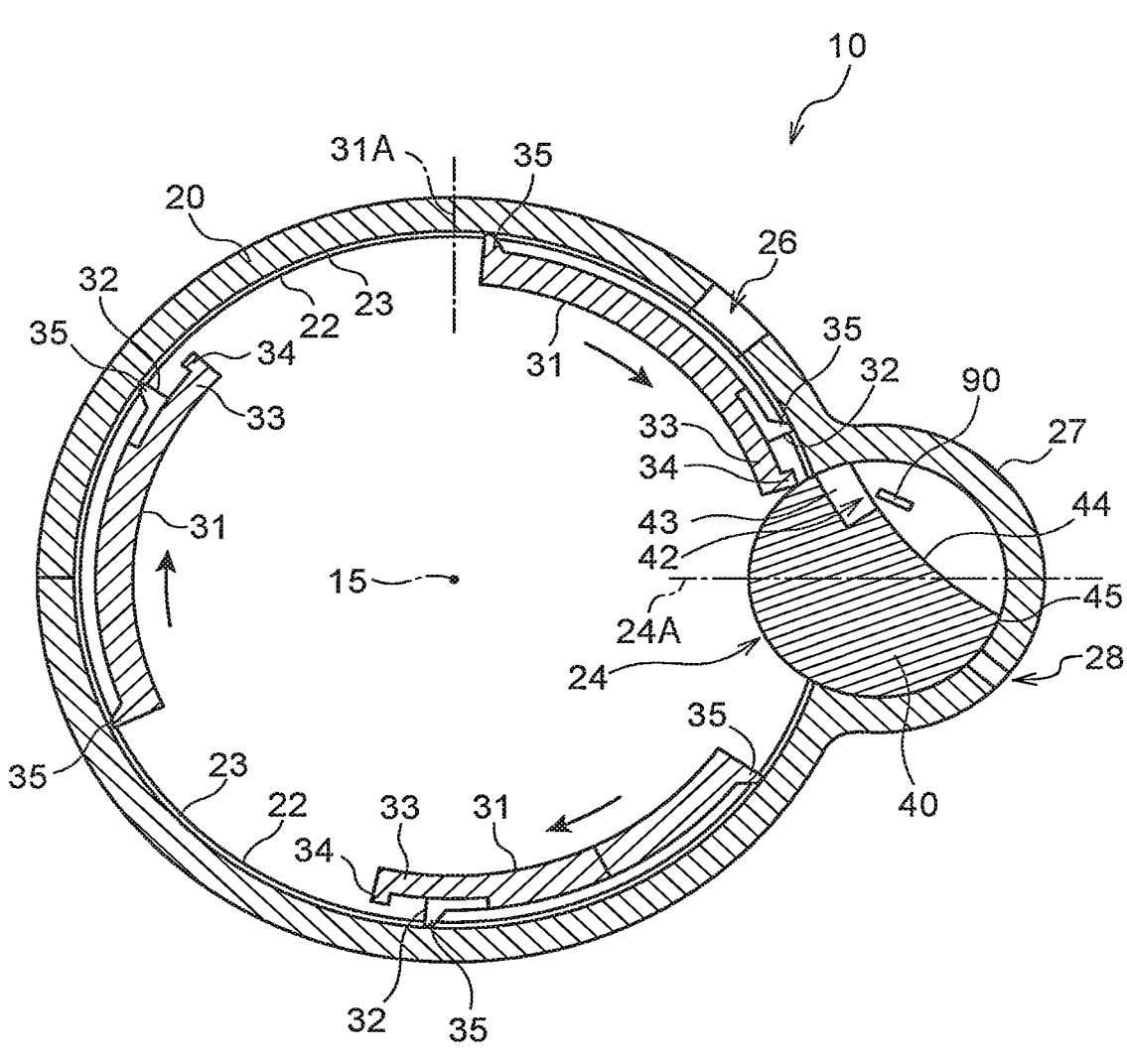
FIG. 16F illustrates a state in which the test strip is discharged, in a cross-sectional view.

When the door member 40 rotates further and reaches the state illustrated in FIG. 16F, the door member 40 again closes the opening portion 24 and the discharge opening 28 by the cutting-off portion 45. Then, the test strip 90 that has been discharged falls down along the inclined surface 44.

Figure 16G:
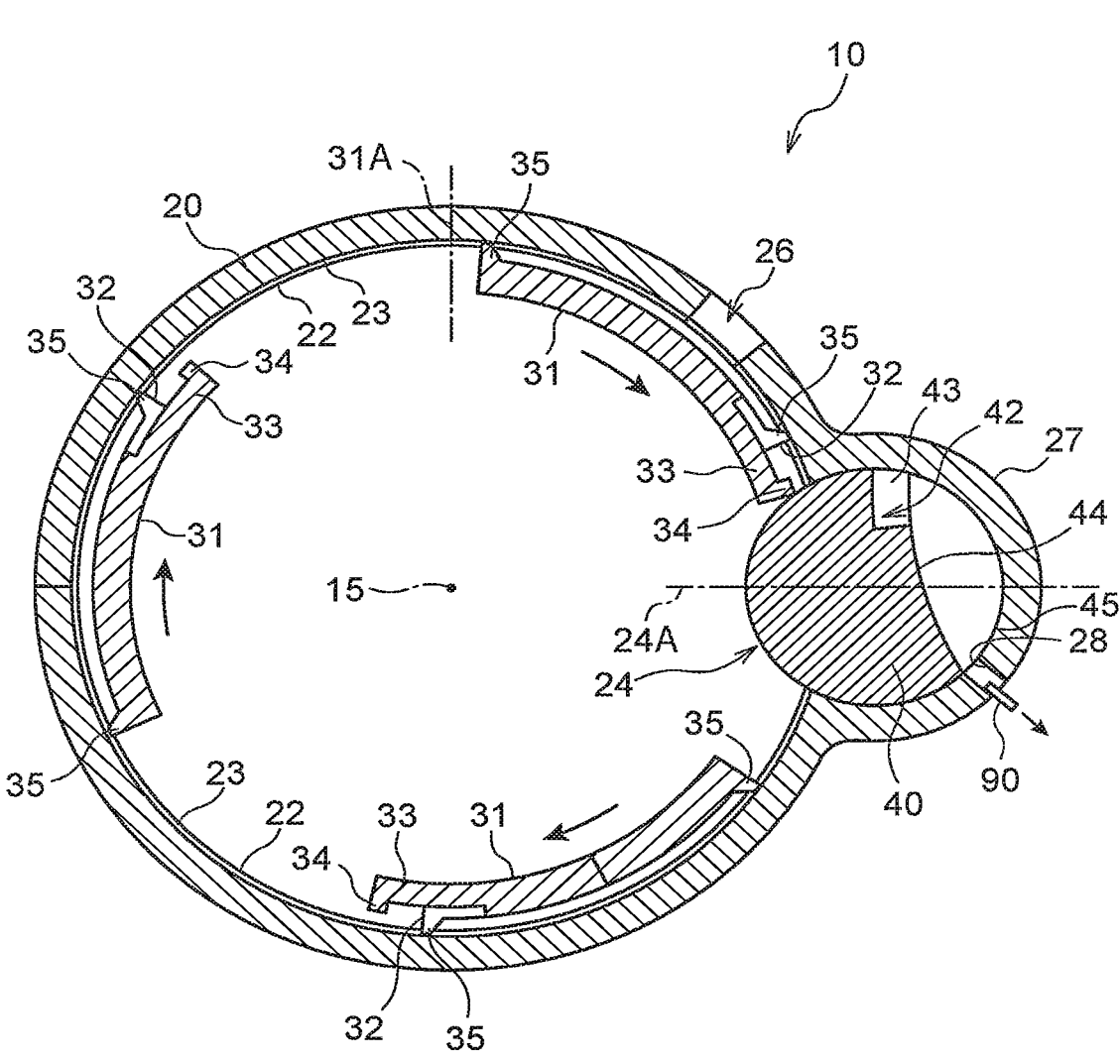
FIG. 16G illustrates a state in which the test strip is discharged, in a cross-sectional view.

When the door member 40 rotates further and reaches the state illustrated in FIG. 16G, the cutting-off portion 45 opens the discharge opening 28 while closing the opening portion 24. The test strip 90 that has been discharged is led along the inclined surface 44 to the opened discharge opening 28. The test strip 90, which is discharged from the discharge opening 28 to the exterior of the door accommodating portion 27, is moved by unillustrated conveying means to the measuring section 5, and is provided to the predetermined measurement thereat.

Figure 17:
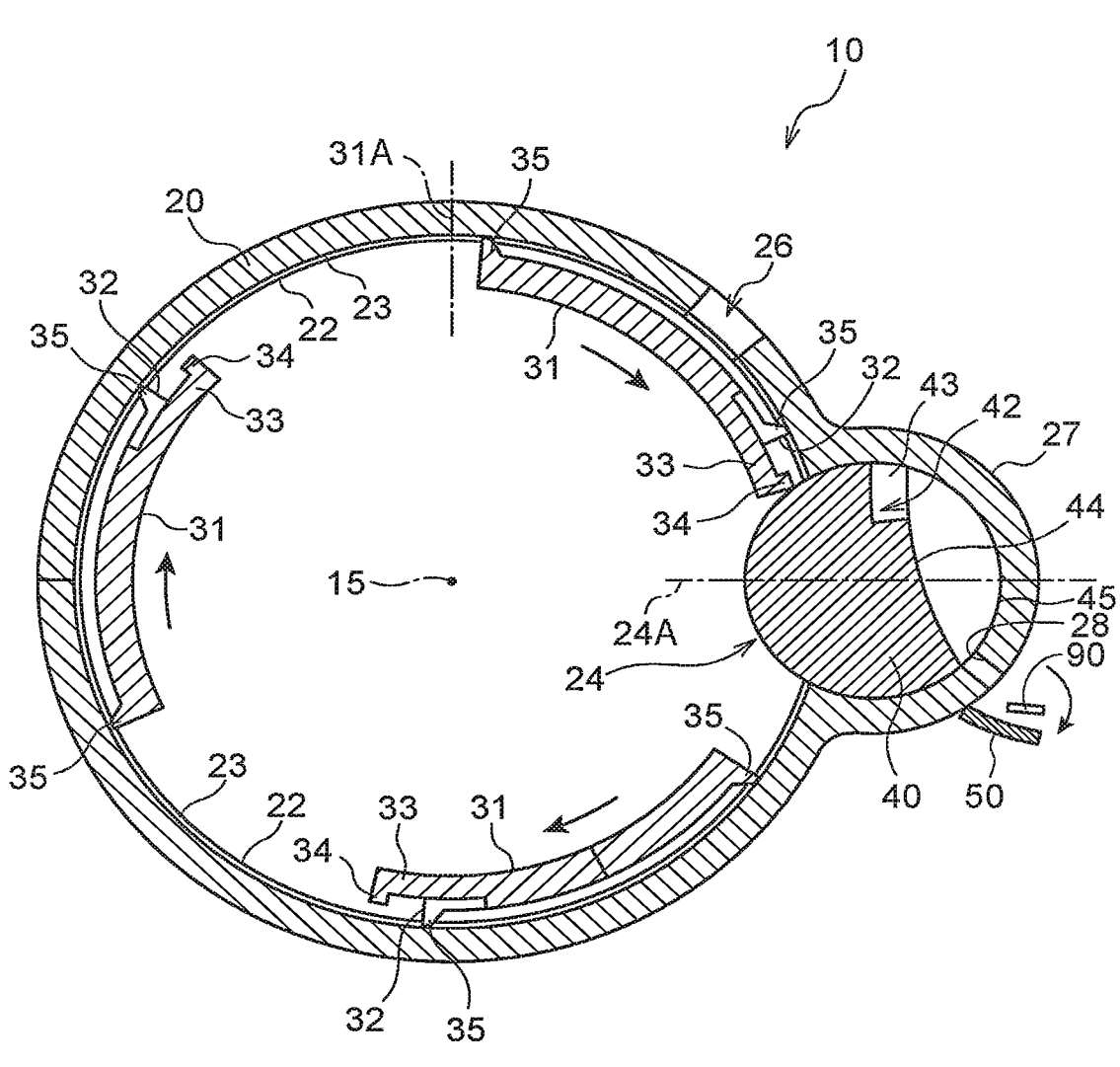
FIG. 17 illustrates a modified example of the exemplary embodiment in a cross-sectional view.

Note that, as in the modified example of the present exemplary embodiment that is illustrated in FIG. 17, an opening/closing member 50 that opens and closes the discharge opening 28 may be provided. This opening/closing member 50 can be opened and closed by the opening/closing operation device 4 in the block drawing of FIG. 13.

In the above-described exemplary embodiment, the door member 40 always closes at least one of the opening portion 24 of the accommodating member 20 and the discharge opening 28 of the door accommodating portion 27. In other words, because the opening portion 24 and the discharge opening 28 are not open at the same time, the test strips 90 accommodated in the accommodating member 20 can always be cut-off from outside air. Thereby, changes in the quality of the test strips 90 due to humidity of the outside air or the like can be prevented.

In addition, only one of the test strips 90 passes through from the gap between the sorting pieces 34 and the cylindrical surface 22, and the test strips 90 that could not pass through fall down when facing downward while the moving member 31 is rotating. Thereby, merely due to the moving member 31 rotating within the accommodating member 20, stress due to pushing is not excessively applied to the test strips 90 that could not pass through. Further, only one of the test strips 90 is naturally grasped by the sorting pieces 34 and the pushing pieces 33, and can be taken out from the opening portion 24.

(2) Other Points

The above-described exemplary embodiment is a form in which the moving member 31 rotates and moves within the accommodating member 20 that is cylindrical, but the present invention is not limited thereto. For example, there may be a form in which the accommodating member 20 is box-shaped, and the moving member 31 that is belt-shaped is bent in the form of bellows and moves at the interior of the accommodating member 20.

Further, the above-described exemplary embodiment is a form in which the door member 40 can open and close by rotating at the interior of the door accommodating portion 27, but the present invention is not limited to this. For example, there may be a form in which the door member 40 opens and closes like a door.

What is claimed is:
1. A test strip container comprising:
an accommodating member having an interior in which a test strip is located;
a moving member located within the interior of the accommodating member that moves the test strip within the interior of the accommodating member;
a door accommodating portion provided on an outer side portion of the accommodating member;
a door member that is provided in the door accommodating portion, the door member being movable between an open position and a closed position for discharging the test strip from the interior of the accommodating member to an exterior area of the test strip container, the door member being configured to block off the interior of the accommodating member and the exterior area of the test strip container from each other; and a discharge opening provided in the door accommodating portion such that, at a time of the door member is moved into the closed position, the door member blocks off the interior of the door accommodating portion from the exterior area of the test strip container and at the time of the door member is being moved into the open position, the test strip is discharged to the exterior area of the test strip container, wherein the discharge opening is configured so as to be able to discharge the test strip while the door member blocks off the interior of the accommodating member from the exterior area of the test strip container, and the discharge opening communicates between an interior portion of the door accommodating portion and exterior area of the test strip container at a lower side of the door accommodating portion where the door member is in the open position, the door member has an inclined surface portion that, at a time of being moved into the open position, provides communication between the interior portion of the door accommodating portion and the discharge opening, and the door member further has a cutting-off portion, which closes the discharge opening at the time of being moved into the closed position and which blocks off the interior portion of the accommodating member from the exterior area of the test strip container at a time of being moved into the open position.

2. The test strip container of claim 1, wherein the test strip falls down from the moving member as the door member is being moved into the open position and slides down the inclined surface portion of the door member to be discharged into to the exterior area of the test strip container.

3. The test strip container of claim 1, wherein:

the test strip is elongated, the accommodating member is shaped as a cylinder whose length in a longitudinal direction is greater than or equal to a length of the test strip, the moving member rotates and moves along an inner peripheral surface of the accommodating member, the door accommodating portion is formed in a shape of a cylinder, having a diameter that is smaller than a diameter of the accommodating member and whose length in a longitudinal direction is greater than or equal to the length of the test strip, the door accommodating portion projects outwardly from a side of the accommodating member, the discharge opening is provided as an opening that runs along a longitudinal direction of the door accommodating portion and has length is greater than or equal to the length of the test strip, the door member is provided along a side surface of the accommodating member in the door accommodating portion in a direction along the longitudinal direction of the accommodating member, the inclined surface of the door member is formed in a shape of a concave surface that has a radius of curvature that equal to a radius of an inner side surface of the accommodating member, and the cutting-off portion of the door member is formed in a shape of a cylindrical, convex surface that has an outer diameter that is equal to a radius of an inner surface of the door accommodating portion.

4. The test strip container of claim 1, wherein:

the moving member moves within the interior of the accommodating member while holding the test strip, and the door member moves between the open and closed positions by rotating within the interior portion of the door accommodating portion, and, at the time of being moved into the open position, the door member applies impact force to the test strip held by the moving member, and causes the test strip to be discharged out from the accommodating member.

5. The test strip container of claim 4, wherein, at the time of being rotated into the open position, the door member applies the impact force to the test strip held by the moving member by causing the inclined surface of the door member to collide with the test strip.

6. A test strip discharging mechanism comprising:

the test strip container of claim 1; and a control section electrically connected to the test strip container that controls rotation of the moving member and the door member, wherein the control section effects control so as to open the discharge opening at a time when the door member is moved into the closed position.

7. The test strip discharging mechanism of claim 6, wherein the control section effects control so that, after stopping movement of the moving member when the moving member approaches the door member, the discharge opening is closed while moving the door member until the door member is in the open position, and, after moving the door member again until a concave surface portion of the door member aligns with an interior surface of the accommodating member, movement of the moving member is restarted.

8. The test strip discharging mechanism of claim 7, comprising a proximity sensor that senses when the moving member has approached the door member, wherein the control section moves the door member into the open position when the proximity sensor senses that the moving member has approached the door member.

*    *    *    *    *